United States Patent [19]

Yamamura et al.

[11] 4,369,178

[45] Jan. 18, 1983

[54] GLUCOSAMINE PEPTIDE DERIVATIVES, THEIR PRODUCTION AND USE

[75] Inventors: Yuichi Yamamura, Takarazuka; Ichiro Azuma, Sapporo; Shigeru Kobayashi, Neyagawa, all of Japan

[73] Assignee: Takeda Chemical Industries, Ltd., Osaka, Japan

[21] Appl. No.: 123,401

[22] Filed: Feb. 21, 1980

[30] Foreign Application Priority Data

Feb. 21, 1979 [JP] Japan .................................. 54-19929

[51] Int. Cl.³ .................... A61K 37/00; C07C 103/52
[52] U.S. Cl. ............................. 424/177; 260/112.5 R
[58] Field of Search ................. 424/177; 260/112.5 R

[56] References Cited

U.S. PATENT DOCUMENTS 4,101,536  7/1978  Yamamura et al. ................. 424/177

*Primary Examiner*—Delbert R. Phillips
*Attorney, Agent, or Firm*—Wegner & Bretschneider

[57] ABSTRACT

Novel glucosamine-peptide derivatives of the formula:

$$R^1-\{NH(CH_2)_n\overset{R^2}{\underset{}{C}}HCO\}_m-O-CH_2$$

(with sugar ring bearing $R^9O$, $OR^8$, $NHCOR$, and $R^3CHCONHCCONHCH(CH_2)_2COOR^7$ with $R^4$ and $CONHR^6$ substituents, $R^5$ group, and (D), (L), (D) configurations)

wherein
 m is 0 or 1;
 n is 0 or an integer of 1 to 9;
 R is lower alkyl which may be substituted with hydroxyl, or aryl;
 $R^1$ is hydrogen or acyl having an acyclic hydrocarbon group, the terminal of which may be substituted with a cyclic hydrocarbon group directly, via a carbonyl group or via an oxygen atom;
 provided that when $R^1$ is hydrogen m is 1;
 $R^2$ is hydrogen or lower alkyl which may form a ring by connecting its terminal with the α-nitrogen atom when n is 0, or hydrogen when n is an integer of 1 to 9;
 $R^3$ is hydrogen or lower alkyl;
 $R^4$ and $R^5$ are each hydrogen or lower alkyl which may be substituted with hydroxyl or benzyloxyl;
 $R^6$ is hydrogen or lower alkyl;
 $R^7$ is alkyl which may be substituted with lower alkoxyl or aralkyl;
 $R^8$ and $R^9$ are each hydrogen, lower alkyl or aralkyl; and
 (D) and (L) each indicate configurations if their respective carbon atoms are asymmetric;

or an acid addition salt thereof, have immunostimulatory activity.

11 Claims, No Drawings

GLUCOSAMINE PEPTIDE DERIVATIVES, THEIR PRODUCTION AND USE

The present invention relates to novel and useful glucosamine derivatives.

The present inventors have succeeded in producing novel glucosamine-peptide derivatives of the formula (I):

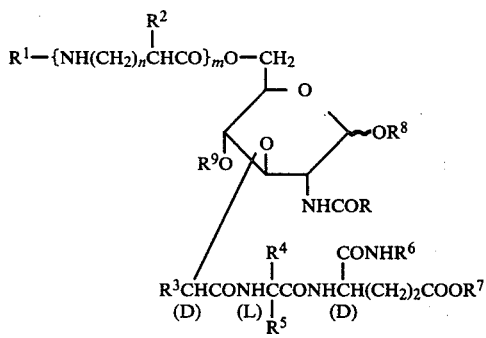

wherein
m is 0 or 1;
n is 0 or an integer of 1 to 9;
R is lower alkyl which may be substituted with hydroxyl, or aryl;
$R^1$ is hydrogen or acyl having an acyclic hydrocarbon group, the terminal of which may be substituted with a cyclic hydrocarbon group directly, via a carbonyl group or via an oxygen atom, provided that when $R^1$ is hydrogen m is 1;
$R^2$ is hydrogen or lower alkyl which may form a ring by connecting its terminal with the α-nitrogen atom when n is 0, or hydrogen when n is an integer of 1 to 9;
$R^3$ is hydrogen or lower alkyl,
$R^4$ and $R^5$ are each hydrogen or lower alkyl which may be substituted with hydroxyl or benzyloxyl;
$R^6$ is hydrogen or lower alkyl;
$R^7$ is alkyl which may be substituted with lower alkoxyl or aralkyl;
$R^8$ and $R^9$ are each hydrogen, lower alkyl or aralkyl; and (D) and (L) each indicate configurations if their respective carbon atoms are asymmetric;
or an acid addition salt thereof.

Further studies on the compounds of the formula (I) have unexpectedly revealed that these compounds and acid addition salts thereof exhibit excellent immunostimulatory activity, especially cell-mediated immunostimulatory activity, and are of value, for example, as anti-infective agents, anti-tumour agents or immunoadjuvants.

Thus, the principal object of the present invention is to provide the novel and useful compounds (I) and acid addition salt thereof which have excellent immunostimulatory activity, and another object is to provide an industrially advantageous process for producing the above compounds of the formula (I) and the salts thereof. Other objects will be made clear from the description and claims presented hereinafter.

Referring to the formula (I), the lower alkyl group for R, $R^2$, $R^3$, $R^4$, $R^5$ and $R^6$ and the alkyl group for $R^7$ may be either straight-chain or branched, and preferably that having up to 6 carbon atoms, e.g., methyl, ethyl, n-propyl, isopropyl, butyl, pentyl, hexyl etc. (these three being straight chains or branched at any position), that having up to 4 carbon atoms being especially preferred. In the case of $R^7$, however, an alkyl group having 18 carbon atoms may also be employed.

The aryl group for R is preferably phenyl and the aralkyl group for $R^7$, $R^8$ and $R^9$ is preferably benzyl, phenethyl etc., the benzene ring contained therein being optionally substituted with halogen atom(s), lower alkyl group(s), nitro group(s), etc.

In the formula (I), $R^1$ is a hydrogen atom, in this case m is 1, or an acyl group having an acyclic hydrocarbon group the terminal of which may be substituted with a cyclic hydrocarbon group directly or via a carbonyl group or an oxygen atom. The acyclic hydrocarbon group here may be either a straight-chain or a branched, and may be either saturated or unsaturated. In the case of the unsaturated hydrocarbon chain, the multiple bonds present may be isolated from each other or conjugated. Where there is a double bond, the main chain may be in either cis or trans form across the double bond. Generally, the acyclic hydrocarbon group having up to 70 carbon atoms is preferred and representative examples of the acyl group include acetyl, propionyl, butyroyl, valeroyl, nonanoyl, parmitoyl, stearoyl, oleoyl, geranylacetyl, digeranylacetyl, farnesylacetyl, geranylgeranylacetyl, di(farnesylfarnesyl)acetyl etc. The cyclic hydrocarbon group which may be present as the substituent at the terminal of the acyclic hydrocarbon group may preferably be an unsaturated 6-membered or fused 10-membered hydrocarbon group, such as phenyl, cyclohexenyl, cyclohexadienyl, dihydronaphthyl etc. The cyclic hydrocarbon group can contain substituent(s) such as lower alkyl group(s) (e.g. methyl, ethyl, isopropyl etc., preferably those having up to 3 carbon atoms), lower alkoxyl group(s) (e.g. methoxy, ethoxy, propoxy etc., preferably those having up to 3 carbon atoms) or/and oxo group(s). Among them, 2,3-dimethoxy-5-methyl-1,4-benzoquinon-6-yl is most preferred. Examples of the acyl group, the terminal of which is substituted with the above cyclic hydrocarbon group, include 3-(2,3-dimethoxy-5-methyl-1,4-benzoquinon-6-yl)propionyl, 6-(2,3-dimethoxy-5-methyl-1,4-benzoquinon-6-yl)hexanoyl, 10-(2,3-dimethoxy-5-methyl-1,4-benzoquinon-6yl)decanoyl, retinoyl, 6-(2,3,5-trimethyl-1,4-benzoquinon-6-yl)-4-methyl-4-hexenoyl, 6-(2,3-dimethoxy-5-methyl-1,4-benzoquinon-6-yl)-4-methyl-4-hexenoyl, 6-(2-methyl-1,4-naphthoquinon-3-yl)-4-methyl-4-hexenoyl, 4-(2,3,5-trimethyl-1,4-benzoquinon-6-yl)-2-methylbutyroyl, 4-(2,3-dimethoxy-5-methyl-1,4-benzoquinon-6-yl)-2-methylbutyroyl, 4-(2-methyl-1,4-naphthoquinon-3-yl)-2-methylbutyroyl, 6-(2,3,5-trimethyl-1,4-benzoquinon-6-yl)hexanoyl, 5-(2-methyl-1,4-naphthoquinon-3-yl)pentanoyl, 3-{[3,4-dihydro-2,5,7,8-tetramethyl-2-(4,8,12-trimethyltridecyl)-2H-1-benzopyran-6-yl]oxycarbonyl}propanoyl etc.

Among the acyl groups described above, the acyl group having an acyclic hydrocarbon group of 11-61 carbon atoms, the terminal of which is not substituted with any cyclic hydrocarbon group, and the acyl group having an acyclic hydrocarbon group of 2-10 carbon atoms, the terminal of which is substituted with the above-mentioned cyclic hydrocarbon group, etc. are preferred.

In the formula (I), n is 0 or an integer of from 1 to 9, and when n is 0, $R^2$ is a hydrogen atom or a lower alkyl group, or may form a 5- to 8-membered ring by connecting its terminal with the α-nitrogen atom. Representative examples of such 5- to 8-membered ring are pyrrolidine, piperazine, perhydroazepine, perhydroazocine etc. When n is an integer of from 1 to 9, $R^2$ is a hydrogen atom.

Among the compounds of the formula (I) above, the compounds in which R and $R^3$ are methyl groups are especially preferred. In addition, when $R^4$ is a hydrogen atom, it is preferred that $R^5$ is a lower alkyl group, a hydroxymethyl group or 1-hydroxyethyl group.

In the above compounds (I), the glucosamine residue is preferably of the D configuration, the $R^3$-substituted acetic acid residue attached to the oxygen atom of 3-position thereof is preferably of the D configuration, the aminoacyl residue, substituted with $R^4$ and $R^5$ when $R^4$ and $R^5$ are not both hydrogen atoms or both same lower alkyl groups, is preferably of the L configuration, and the monoaminodicarboxylic acid residue is preferably the D-isoglutamine residue.

The preferable compounds of this invention are shown by the general formula (I'):

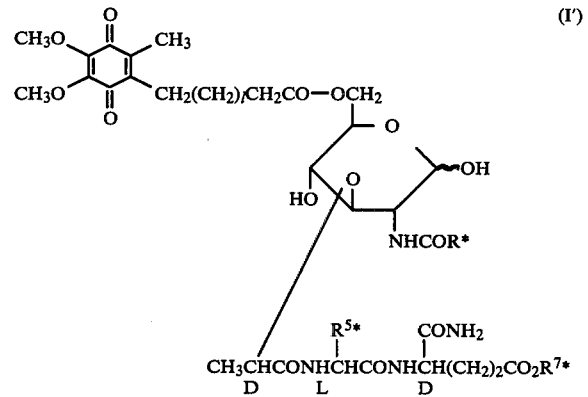

wherein
l is an integer of 0 to 7;
$R^*$ is $C_{1-4}$ alkyl;
$R^{5*}$ is $C_{1-4}$ alkyl which may be substituted with hydroxyl;
$R^{7*}$ is $C_{1-4}$ alkyl; and
D and L each indicate the configuration of the carbon atoms.

Examples of the preferred compounds among the glucosamine-peptide derivatives in accordance with the present invention are as follows:
methyl 2-{2-acetamido-2-deoxy-6-0-[10-(2,3-dimethoxy-5-methyl-1,4-benzoquinon-6-yl)decanoyl-L-leucyl]-D-glucopyranos-3-0-yl}-D-propionyl-L-valyl-D-isoglutaminate,
methyl 2-{2-acetamido-2-deoxy-6-0-[10-(2,3-dimethoxy-5-methyl-1,4-benzoquinon-6-yl)decanoyl]glycyl-D-glucopyranos-3-0-yl}-D-propionyl-L-valyl-D-isoglutaminate,
isopropyl 2-{2-acetamido-2-deoxy-6-0-[10-(2,3-dimethoxy-5-methyl-1,4-benzoquinon-6-yl)decanoyl]-D-glucopyranos-3-0-yl}-D-propionyl-L-valyl-D-isoglutaminate,
2-methoxyethyl 2-{2-acetamido-2-deoxy-6-0-[10-(2,3-dimethoxy-5-methyl-1,4-benzoquinon-6-yl)decanoyl]-D-glucopyranos-3-0-yl}-D-propionyl-L-valyl-D-isoglutaminate,
methyl 2-{2-acetamido-2-deoxy-6-0-[10-(2,3-dimethoxy-5-methyl-1,4-benzoquinon-6-yl)decanoyl]-D-glucopyranos-3-0-yl}-D-propionyl-L-valyl-D-isoglutaminate,
methyl 2-{2-acetamido-2-deoxy-6-0-[10-(2,3-dimethoxy-5-methyl-1,4-benzoquinon-6-yl)decanoyl]-D-glucopyranos-3-0-yl}-D-propionyl-L-seryl-D-isoglutaminate, etc.

The compounds (I) are basic or neutral depending on the kind of the substituent. When basic, they form acid addition salts with an inorganic acid, e.g. hydrochloric acid, hydrobromic acid, phosphoric acid, nitric acid, sulfuric acid etc., an organic carboxylic acid, e.g. acetic acid, propionic acid, maleic acid, succinic acid, malic acid, citric acid, tartaric acid, salicylic acid, nicotinic acid etc., or an organic sulfonic acid, e.g. methanesulfonic acid, p-toluenesulfonic acid etc. The compounds (I) may be used as the physiologically acceptable salts with these acids.

The compounds (I) of the present invention have low toxicity and potent activity of stimulating the immunological functions. Particularly, the compounds (I) significantly enhance the cell-mediated immunity which plays a major role for antiinfection. This can be established by the following experiments.

The ability of the compound (I) to stimulate the cell-mediated immunity of recipient hosts can be established by their immunoenhancing effect on the induction of delayed-type hypersensitivity to azobenzenearsonate N-acetyl-L-tyrosine (ABA-N-Ac-Tyr) in guinea pigs. Thus, a mixed solution of ABA-N-Ac-Tyr (50 μg per animal) and the compound (I) of this invention (10–200 μg per animal) in phosphate-buffered saline was admixed with Freund's incomplete adjuvant to prepare a water-in-oil emulsion and guinea pigs (Hartley strain) were immunized by injecting the emulsion into the footpad of each animal in a dose of 0.05 ml. After 2 weeks the back of each animal was shaved and ABA-bacterial α-amylase [ABA-BαA] (100 μg) was intraperitoneally administered. After 24 and 48 hours, the diameters of skin reactions (erythema and induration) were measured. These diameters serve as a measure of cell-mediated immunity.

As a control, when a solution of ABA-N-Ac-Tyr, which is the antigen, alone in phosphate-buffered saline was admixed with Freund's incomplete adjuvant to prepare a water-in-oil emulsion and this emulsion was similarly administered, there was induced no delayed type hypersensitivity to ABA-N-Ac-Tyr. This experiment indicates that the compounds in accordance with the present invention possess strong immunostimulatory activity on cellular immune reactions (delayed hypersensitivity).

The cell-mediated immunostimulatory activity of the compounds (I) is also evident from the fact that they are able to markedly amplify the onset of cytotoxicity [The induction of lymphocytes specifically toxic to target cells (cancer cells)]. Thus, C57BL/6J mice (H-a[b]) are intraperitoneally injected with Mastocytoma P815-X2(H-a[d]) cells, with or without one of the compounds according to this invention as a solution or suspension in phosphate-buffered saline. On day 11 after this immunization, the spleen of each mouse is enucleated and the population of the T-cell (killer-T cell) cytotoxic to the target cells produced in the spleen is determined by the method of Brunner (Immunology, 18, 501–515). The concurrent administration of a compounds (I) and said Mastocytoma cells resulted in a marked increase in the killer-T cell population in the spleen. While a cancer therapy designed to reject cancer cells, which are nonautologous cells, by increasing the immunological responsiveness of the patient has been widely practiced in recent years, it is thought to be the killer-T cell that plays a major role in this therapy. In this sense, the killer-T population as stimulated by the administration of the compounds (I) may be regarded as a measure of antitumour activity.

For example, 100–300 μg of the compounds according to the present invention were dissolved or suspended in phosphate-buffered saline and mixed with $5 \times 10^5$ tumor cells Meth-A, followed by the intracutaneous administration to female Balb/C mice. The effects to inhibit the growth of Meth-A were examined at 1 week intervals until the 4th week after the administration. As a result, as shown in Table 1, strong inhibiting effects were observed.

TABLE 1

| Test sample | Dosage (μg) | The number of tumor-free mice/the number of mice tested | | | |
|---|---|---|---|---|---|
| | | 1 | 2 | 3 | 4(week) |
| Methyl 6-O-(QS-10-L-leucyl)-N—acetylmuramyl-L-valyl-D-isoglutaminate (Example 41) | 100 | 10/10 | 6/10 | 5/10 | 5/10 |
| Methyl 6-O-(QS-10-glycyl)-N—acetylmuramyl-L-valyl-D-isoglutaminate (Example 40) | 100 | 10/10 | 9/10 | 9/10 | 8/10 |
| Methyl 6-O-(QS-10)-N—acetylmuramyl-L-valyl-D-isoglutaminate (Example 36) | 100 | 8/10 | 4/10 | 4/10 | 4/10 |
| Control (1) 6-O-(QS-10)-N—acetylmuramyl-L-valyl-D-isoglutamine | | 0/10 | 0/10 | 0/10 | 0/10 |
| Control (2) | — | 0/10 | 0/10 | 0/10 | 0/10 |

By virtue of the aforementioned properties, the compounds (I) according to this invention can be employed for the treatment of many diseases attributable to cell-mediated immunity depressions, for example as anti-infective agents (e.g., for suppressing enteritis and pneumonia).

On the one hand, because the compound (I) are capable of stimulating the immunogenicity of an antigen when used in combination therewith, they are suitable for use as an admixture with various antigens for the production of diagnostic and therapeutic antisera. Moreover, the compounds (I) can be employed for the purpose of potentiating the immunity already latent in the body, without concomitant addition of antigens. Therefore, the compounds (I) are particularly effective in the treatment of hosts with chronic and acute infectious disease, hosts with congenital immunodeficiency, hosts who acquired impaired immunity, for example, in the course of a serious primary disease at an advanced age.

The compounds (I) can thus be administered to warmblooded animals (e.g. man; laboratory animals such as mouse, guinea pig, rat, etc.; pet animals such as dog, cat, etc.) either enterally, e.g. orally or rectally, or parenterally. The dosage depends on the individual conditions of the animal, its species and age and the dosage form used. When, for example, the compound is used as an injectable isotonic solution, e.g. an isotonic aqueous solution such as a salt-containing solution or a glucose solution, for subcutaneous, intracutaneous or intramuscular administration, the preferred dosage as antiinfectious agents may range from about 1 to 500 μg/kg/day (as the anhydrate of the compound) and, particularly, from about 5 to 30 μg/kg/day (on the same basis).

For such parenteral administration, the compound may also be administered in the form of a stabilized water-in-oil emulsion, the oil being preferably of the vegetable or animal origin. Such a vegetable or animal oil emulsion may comprise about 5 to 100 volume parts of the isotonic aqueous solution and one volume part of a metabolizable vegetable or animal oil, supplemented with an emulsion stabilizer, for instance.

For administration by the oral route, the compound may be formulated with a pharmaceutically acceptable excipient and used as sugar-coated tablets, capsules, etc., the dosage in such forms being between about 40 and 4000 μg/kg/day.

The compounds of the formula (I) may be easily obtained from compounds of the formula (II):

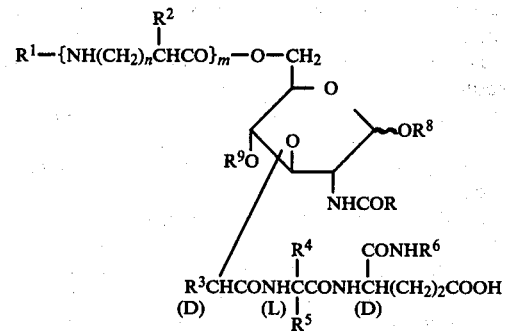

(II)

wherein m, n, R, $R^1$, $R^2$, $R^3$, $R^4$, $R^5$, $R^6$, $R^8$, $R^9$, (D) and (L) are as defined above, by esterifying in a known manner. The modes of the esterification include a reaction with a lower alcohol in the presence of hydrogen chloride, a reaction with a reaction product of a lower alcohol and thionyl chloride, a reaction with diazomethane, or a reaction of compound (II) activated by 6-chloro-1-p-chlorobenzenesulfonyloxybenzotriazole with a lower alcohol etc.

Alternatively, the compounds of the formula (I) in accordance with the present invention may be obtained by condensing a compound of the formula (III)

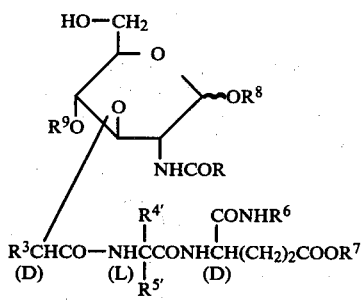

(III)

wherein R, $R^3$, $R^6$, $R^7$, $R^8$ and $R^9$ are as defined above and $R^{4'}$ and $R^{5'}$ are the same as $R^4$ and $R^5$, respectively, except that any hydroxyl group if present therein is protected, with a compound of the formula (IV)

$$R^{1'}-OH \qquad (IV)$$

wherein $R^{1'}$ is the same as $R^1$ excluding hydrogen atom, or with a compound of the formula (V)

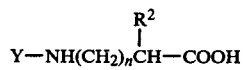

(V)

wherein n and $R^2$ are as defined above and Y is a protecting group for the amino group, followed by, if necessary, the elimination of the protecting group.

In the above formula (III), for the protecting group for the hydroxyl group included in the groups designated by $R^{4'}$ and $R^{5'}$, any known protecting group which is easily removable may be used, such as alkyl groups (e.g. tert-butyl group), tetrahydropyranyl group, benzoylcarbonyl group, lower alkanoylcarbonyl groups etc., especially benzyl group which may optionally be substituted with a halogen atom(s), a nitro group(s), a lower alkyl group(s), a lower alkoxy group(s) etc. being preferably employed.

In the above formula (V), for the protecting group for the amino group designated Y, any of the easily removable protecting groups known in the field of peptide chemistry may be employed. For example, benzyloxycarbonyl (carbobenzoxy) group, p-methoxybenzylcarbonyl group, p-methylbenzylcarbonyl group, tert-butoxycarbonyl group, tertamyloxycarbonyl group, p-biphenylisopropyloxycarbonyl group, o-nitrophenylsulfenyl group, trityl group etc. are conveniently employed.

The condensation of the above compound (III) and the compound (IV) or the compound (V) may be conducted in a known manner. For example, it is preferred to activate the carboxyl group in the compound (IV) or the compound (V) and then react it with the compound (III).

The activated carboxyl group includes an activated ester and an acid anhydride.

Examples of the activated ester are p-nitrophenyl ester, N-hydroxysuccinimide ester, N-hydroxy-5-norbornene-2,3-dicarboxyimide ester, 1-hydroxybenzotriazole ester which is unsubstituted or substituted with a halogen group(s), a halomethyl group(s) or methoxy group(s), etc.

The acid anhydride is preferably a mixed acid anhydride an acid amide, e.g. imidazolide, isoxazolide etc.

In the reaction by an activated ester, an organic base such as triethylamine, N-methylmorpholine, N-ethylmorpholine or 1-hydroxybenzotriazole may be co-present, if necessary.

The activation of the carboxyl group may also be effected by a direct reaction of the compound (IV) or the compound (V) with N,N'-dicyclohexylcarbodiimide.

The reaction temperature is generally from about 0° C. to about 80° C., preferably about 5°–50° C. If desired, the reaction can be carried out at a temperature outside the above range.

Generally, the reaction proceeds in a solvent. Examples of the solvent which may be used are ethers such as tetrahydrofuran, dioxane etc., esters such as ethyl acetate, isoamyl acetate etc., N-alkylamides such as N,N-dimethylformamide, N-methyl-2-pyrrolidone, N,N-dimethylacetamide etc., pyridine, dimethylsulfoxide, hexamethylphosphoramide etc.

The above compound (III) reacts with the compound (IV) or the compound (V) stoichiometrically, but it is, of course, unnecessary that the two components be present in equimolar amounts in the reaction system, and generally the compound (IV) or the compound (V) or their reactive derivative is used in an amount of about 1–5 moles, preferably 1–2 moles per one mole of the compound (III). The ratio of the two components can be chosen according to the combination of the starting materials and other conditions in order to obtain good results.

The unreacted starting materials can be appropriately recovered and used as the starting materials again.

After the reaction, the protecting group may be removed in a known manner. For example, it may be removed by hydrogenation in the presence of a noble metal catalyst (e.g. platinum or palladium), or by acid hydrolysis.

The thus obtained compound (I) may be isolated as the free base or as the above-mentioned salt using a known purification means such as extraction, phase transfer, various chromatographies, crystallization, recrystallization, reprecipitation etc.

In addition, if the compound obtained by the above reaction is the compound of the formula (VI)

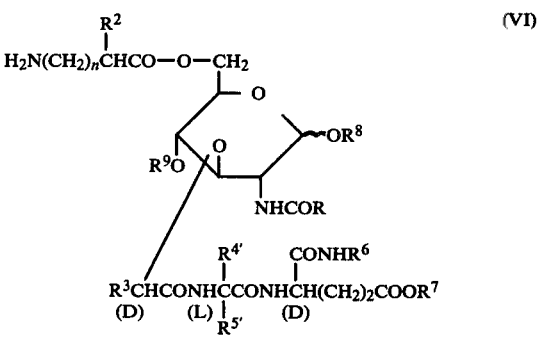

(VI)

wherein m, R, $R^2$, $R^3$, $R^6$, $R^7$, $R^8$, $R^9$, $R^{4'}$ and $R^{5'}$ are as defined above, it may further be condensed with the compound (IV), and subsequently, if necessary, the protecting group may be removed. The condensation reaction of the compound (IV) and the compound (VI) may be conducted similarly as in the condensation reaction of the compound (III) and the compound (IV) or the compound (V), and the subsequent removal of the protecting group may be conducted in a similar manner as above.

The following examples are intended to illustrate this invention in further detail and should by no means be construed as limiting the scope of the invention.

In the following examples, the substituent represented by the formula (VII):

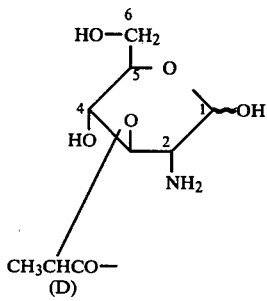

is referred to as muramyl and the positions of the substituents in the sugar moiety are given the numerals of the carbon atoms shown in the formula according to the general nomenclature for saccharides. For example, the group (VIII):

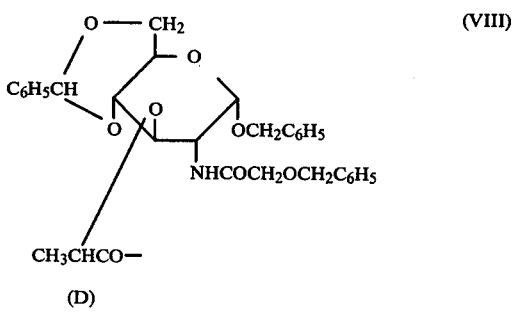

is abbreviated to 1-α-O-benzyl-4,6-O-benzylidene-N-benzyloxyacetyl muramyl.

In addition, for the sake of simplicity, 10-(2,3-dimethoxy-5-methyl-1,4-benzoquinon-6-yl)decanoic acid and 3-(2,3-dimethoxy-5-methyl-1,4-benzoquinon-6-yl)-propionic acid are expressed as QS-10-OH and QS-3-OH, respectively. Accordingly, QS-10-stands for 10-(2,3-dimethoxy-5-methyl-1,4-benzoquinon-6-yl)decanoyl group and QS-3-stands for 3-(2,3-dimethoxy-5-methyl-1,4-benzoquinon-6-yl) propionyl group.

More particularly, for example, methyl 1-α-O-benzyl-6-O-(QS-10)-N-acetylmuramyl-O-benzyl-L-seryl-D-isoglutaminate stands for methyl 2-{benzyl 2-acetamido-2-deoxy-6-O-[10-(2,3-dimethoxy-5-methyl-1,4-benzoquinon-6-yl)decanoyl]-α-I-glucopyranosid-3-O-yl}-D-propionyl-O-benzyl-L-seryl-D-isoglutaminate (IX), and methyl 6-O-[(QS-10)-11-aminoundecanoyl]-N-acetylmuramyl-L-valyl-D-isoglutaminate stands for methyl 2-{2-acetamido-2-dexoy-6-O-[10-(2,3-dimethoxy-5-methyl-1,4-benzoquinon-6-yl)-decanoyl-11-aminoundecanoyl]-D-glucopyranos-3-O-yl}-D-propionyl-L-valyl-D-isoglutamineate (X).

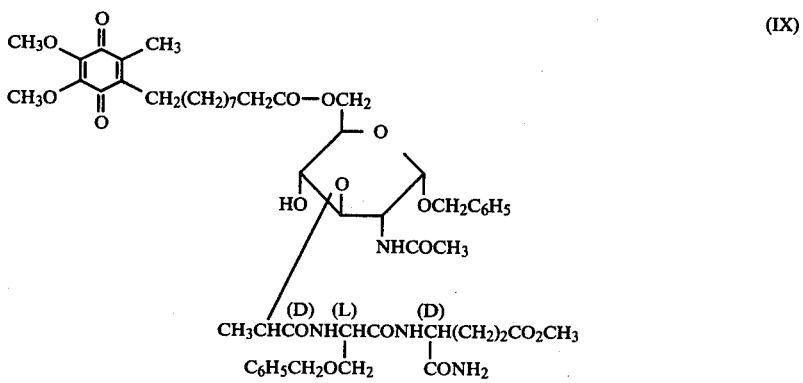

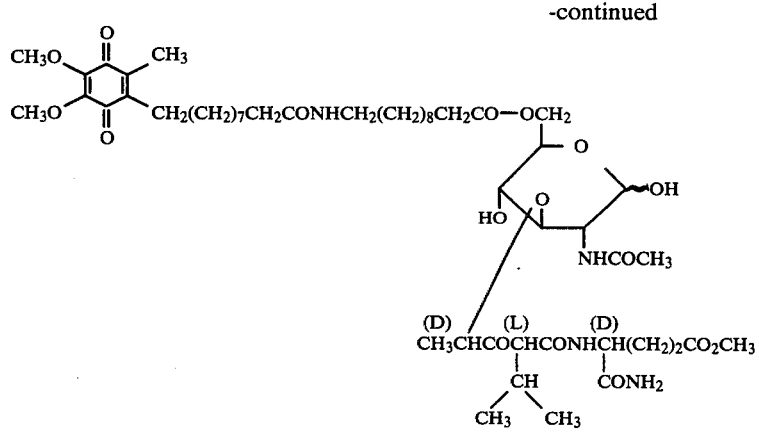

EXAMPLE 1

6-O-(L-Leucyl)-N-acetylmuramyl-α-aminoisobutylyl-D-isoglutamine (180 mg, 0.3 mmol) was dissolved in methanol (15 ml). To this solution was added a solution of diazomethane in ether under ice-cooling until the yellow color of the reaction mixture was retained for 10 minutes. Excess diazomethane was decomposed by adding a few drop of acetic acid and then the solvent was distilled off. The residue was dissolved in a small amount of a mixture of 0.1 N acetic acid and ethanol (2:3, v/v) and chromatographed on a Sephadex LH-20 column (1.5×90 cm). The column was developed by the same solvent. The fractions containing the pure, desired product (76 ml–88 ml) were collected, concentrated and freeze dried to obtain methyl 6-O-(L-leucyl)-N-acetylmuramyl-α-aminoisobutylyl-D-isoglutaminate (66 mg.) $[\alpha]_D^{23}$ +30.5° (C 0.5, N,N-dimethylformamide (hereinafter referred to as DMF)). Rf=0.23 (ethyl acetate:pyridine:acetic acid:water=30:10:3:5, v/v, silica gel plate; the Rf value obtained under these conditions is hereinafter referred to as $R_f^1$).

Elemental analysis for $C_{27}H_{47}O_{12}N_5.CH_3COOH.H_2O$: Calculated: C, 48.93; H, 7.51; N, 9.84. Found: C, 49.08; H, 7.54 N, 9.69.

EXAMPLE 2

Methyl 6-O-(L-leucyl)-N-acetylmuramyl-α-aminoisobutylyl-D-isoglutaminate (50 mg, 0.079 mmol) was dissolved together with QS-10-OH p-nitrophenyl ester (41.7 mg, 0.088 mmol) and N-ethylmorpholine (hereinafter referred to as NEM, 0.012 ml) in DMF (0.5 ml). After being stirred at room temperature for 60 hours, the mixture was concentrated to dryness. The residue was purified by the column chromatography on silica gel (15 g) (column size 2×12 cm: elution solvent: ethyl acetate/pyridine/acetic acid/water=30:10:3:5, v/v). The fractions containing the pure desired product (40 ml to 60 ml) were collected, and the solvent was distilled off. The residue was further purified by the column chromatography on Sephadex LH-20 (column size 1.5×90 cm; elution solvent: 0.1 N acetic acid/ethanol=2:3, v/v). The fractions of the eluate from 72 ml to 80 ml were collected and the solvent was evaporated. The residue was freeze-dried from t-butanol to obtain pure methyl 6-O-(QS-10-L-leucyl)-N-acetylmuramyl-α-aminoisobutylyl-D-isoglutaminate (36 mg). $[\alpha]_D^{23}$ +20.8° (C 0.5, ethanol), $R_f^1$=0.81, $R_f$=0.32 (chloroform:methanol:acetic acid=18:2:1, v/v; silica gel plate; the Rf value obtained under these conditions is hereinafter referred to as $R_f^2$).

Elemental analysis for $C_{47}H_{73}O_{17}N_5$: Calculated: C, 57.07; H, 7.60; N, 7.23. Found: C, 56.82; H, 7.90; N, 7.03.

EXAMPLE 3

6-O-(L-leucyl)-N-acetylmuramyl-L-valyl-D-isoglutamine (190 mg, 0.3 mmol) was reacted with diazomethane in methanol as described in Example 1 to give methyl 6-O-(L-leucyl)-N-acetylmuramyl-L-valyl-D-isoglutaminate (94 mg), $[\alpha]_D^{23}$ +46.7° (C 0.5, DMF). $R_f^1$=0.28.

Elemental analysis for $C_{28}H_{49}O_{12}N_5.CH_3COOH$: Calculated: C, 50.91; H, 7.55; N, 9.90. Found: C, 50.56; H, 7.77; N, 9.81.

EXAMPLE 4

Methyl 6-O-(L-leucyl)-N-acetylmuramyl-L-valyl-D-isoglutaminate (5.18 mg, 0.08 mmol) and QS-10-OH p-nitrophenyl ester (41.7 mg, 0.088 mmol) were reacted in DMF in the presence of NEM (0.012 ml) at room temperature for 60 hours. The resulting mixture was then treated and purified as in Example 2 to obtain methyl 6-O-(QS-10-L-leucyl)-N-acetylmuramyl-L-valyl-D-isoglutaminate (32 mg). $[\alpha]_D^{23}$ +21.0° (C 0.5, ethanol). $R_f^1$=0.86, $R_f^2$=0.38.

Elemental analysis for $C_{47}H_{75}O_{17}N_5.H_2O$: Calculated: C, 56.44; H, 7.76; N, 7.00. Found: C, 56.49; H, 7.69; N, 6.85.

EXAMPLE 5

(I) 1-α-O-Benzyl-4,6-O-benzylidene-N-benzyloxyacetylmuramic acid (4.0 g, 6.94 mmol) and N-hydroxy-5-norbornene-2,3-dicarboximide (hereinafter referred to as HONB, 1.37 g, 7.6 mmol) were dissolved in DMF (30 ml). To this solution was added N,N'-dicyclohexylcarbodiimide (hereinafter referred to as DCC, 1.57 g, 7.63 mmol) under ice-cooling and the resulting mixture was stirred under ice-cooling for one hour and then at room temperature for 15 hours. Then the precipitate was filtered and the solvent was distilled off. The residue was dissolved in ethyl acetate (100 ml) and the resulting solution was washed with a 5% aqueous sodium bicarbonate solution and then with water. The organic layer was dried over anhydrous sodium sulfate and evaporated. To the crystalline residue was added petroleum ether, and the mixture was cooled and filtered to obtain 1-α-O-benzyl-4,6-O-benzylidene-N-benzyloxyacetylmuramic acid HONB ester (5.10 g). m.p. 98°–99° C. $[\alpha]_D^{27}$ +69.0° C. (C 0.5, DMF). $R_f$=0.76

(chloroform; methanol=19:1, v/v; silica gel plate; the $R_f$ value obtained under these conditions is referred to as $R_f^3$).

Elemental analysis for $C_{41}H_{42}O_{11}N_2$: Calculated: C, 66.65; H, 5.73; N, 3.79. Found: C, 66.64; H, 5.99; N. 3.77.

(II) D-glutamic acid γ-methyl ester hydrochloride (19.7 g, 0.1 mol) was dissolved together with triethylamine (hereinafter referred to as TEA; 14 ml) in water (55 ml). To this was added a solution of S-t-butyloxycarbonyl-4,6-dimethyl-2-mercaptopyrimidine (26.4 g, 0.11 mol) in DMF (55 ml) and, TEA (14 ml), and the mixture was stirred at room temperature for 60 hours. Water (200 ml) was then added to the reaction mixture and the mixture was extracted with ether (150 ml×2). The aqueous layer was acidified to pH 2 by adding 3 N hydrochloric acid under ice-cooling, and extracted with ethyl acetate (150 ml×2). The ethyl acetate extracts were combined and washed with 1 N hydrochloric acid and then with water. The extract was dried over anhydrous sodium sulfate and evaporated to obtain oily t-butyloxycarbonyl-D-glutamic acid γ-methyl ester (23.5 g).

A part of the oil (261 mg, 1 mmol) was dissolved in ether (5 ml). To this was added dicyclohexylamine (180 mg, 1 mmol) and the solution was cooled. The resulting precipitate was filtered to obtain t-butyloxycarbonyl-D-glutamic acid γ-methyl ester dicyclohexylamine salt for an analytical sample. m.p. 155° C. $[\alpha]_D^{23}$ −10.2° (C 0.5, methanol). $R_f^2 = 0.68$.

Elemental analysis for $C_{23}H_{42}O_6N_2$: Calculated: C, 62.41; H, 9.57; N, 6.33. Found: C, 62.45; H, 9.61; N, 6.17.

(III) t-Butyloxycarbonyl-D-glutamic acid γ-methyl ester (oil, 13.1 g, 50 mmol) and N-hydroxysuccinimide (7.0 g, 55 mmol) were dissolved in acetonitrile (150 ml). To this solution was added DCC (11.3 g, 55 mmol) under ice-cooling, and the mixture was stirred under ice-cooling for 3 hours and then at room temperature for 12 hours, filtered and evaporated. The residue was dissolved in tetrahydrofuran (50 ml). To this solution was added ammonia water (18 ml) dropwise under ice-cooling. After being stirred under ice-cooling for 30 minutes and then at room temperature for 30 minutes, the reaction mixture was concentrated to dryness. The residue was extracted by ethyl acetate (250 ml) and the resulting extract was washed with a 5% aqueous sodium bicarbonate solution, a 10% citric acid solution and water successively. After being dryed over anhydrous sodium sulfate, the extract was evaporated. The residual crystals were recrystallized from ethyl acetate/petroleum ether to obtain methyl t-butyloxycarbonyl-D-isoglutaminate (6.4 g). m.p. 129°–130° C. $[\alpha]_D^{23}$ −4.2° (C 0.5, DMF). $R_f^2 = 0.61$, $R_f^3 = 0.22$.

Elemental analysis for $C_{11}H_{20}O_5N_2$: Calculated: C, 50.75; H, 7.74; N, 10.76. Found: C, 51.08; H, 7.95; N, 10.76.

(IV) t-Butyloxycarbonyl-L-valine (15.2 g, 70 mmol) and HONB (13.8 g, 77 mmol) were dissolved in a mixture of acetonitrile (300 ml) and DMF (30 ml). To this solution was added DCC (15.9 g, 77 mmol) under ice-cooling and the mixture was stirred for one hour and then at room temperature for 4 hours. The precipitate was filtered and the solvent was distilled off. The residue was dissolved in ethyl acetate (300 ml) and washed with a 5% aqueous sodium bicarbonate solution and then with water. After being dryed over anhydrous sodium sulfate, the mixture was evaporated. To the residue was added petroleum ether under cooling, and the formed crystals were filtered to obtain t-butyloxycarbonyl-L-valine HONB ester (25.6 g). m.p. 120°–122° C. $R_f^3 = 0.72$.

(V) Methyl t-butyloxycarbonyl-D-isoglutaminate (5.0 g, 19.1 mmol) was dissolved in trifluoroacetic acid (20 ml) and the mixture was allowed to stand at room temperature for 15 minutes. Trifluoroacetic acid was then evaporated and the oily residue was washed thoroughly with ether and dried over sodium hydroxide pellets in a desiccator. The resulting methyl D-isoglutaminate trifluoroacetic acid salt was dissolved in acetonitrile (40 ml). To this was added TEA (5.6 ml) and t-butyloxycarbonyl-L-valine HONB ester (7.22 g, 19.1 mmol) under cooling. After being stirred at room temperature for 15 hours, the mixture was evaporated. The residue was extracted by ethyl acetate (200 ml) and the extract washed with a 5% aqueous sodium bicarbonate solution, a 10% citric acid solution and water successively. During this purification procedure a part of the desired product crystallized out. After filtration, the filtrate was dried over anhydrous sodium sulfate and the solvent was evaporated. The residue and the above mentioned crystals were combined and recrystallized from ethyl acetate/petroleum ether to obtain methyl t-butyloxycarbonyl-L-valyl-D-isoglutaminate (5.8 g). m.p. 117°–119° C. $[\alpha]_D^{23}$ +8.55° (C 0.5, DMF). $R_f^2 = 0.78$.

Elemental analysis for $C_{16}H_{29}O_6N_3$: Calculated: C, 53.46; H, 8.13; N, 11.69. Found: C, 53.72; H, 8.10; N, 11.44.

(VI) Methyl t-butyloxycarbonyl-L-valyl-D-isoglutaminate (359 mg, 1 mmol) was dissolved in trifluoroacetic acid (5 ml) and the mixture was allowed to stand at room temperature for 20 minutes. After evaporation, ether was added to the residue. The resulting trifluoroacetic acid salt, after being triturated and filtered, was dissolved in acetonitrile (10 ml) and neutralized with TEA (0.17 ml) under cooling. To this was added a solution of 1-α-O-benzyl-4,6-O-benzylidene-N-benzyloxyacetylmuramic acid HONB ester (737 mg, 1 mmol) in acetonitrile (10 ml), and the mixture was stirred at room temperature for 15 hours. The resulting crystals were filtered and washed with hot acetonitrile to obtain methyl 1-α-O-benzyl-4,6-O-benzylidene-N-benzyloxyacetylmuramyl-L-valyl-D-isoglutaminate (545 mg). m.p. 210°–212° C. $[\alpha]_D^{23}$ +62.3° (C 0.5, DMF). $R_f^2 = 0.71$, $R_f = 0.85$ (chloroform:acetone:methanol=10:3:2, v/v; silica gel plate; the $R_f$ value obtained under these conditions is hereinafter referred to $R_f^4$).

Elemental analysis for $C_{43}H_{54}O_{12}N_4$: Calculated: C, 63.07; H, 6.65; N, 6.84. Found: C, 62.92; H, 6.78; N, 6.55.

(VII) Methyl 1-α-O-benzyl-4,6-O-benzylidene-N-benzyloxyacetylmuramyl-L-valyl-D-isoglutaminate (520 mg, 0.64 mmol) was dissolved in 75% acetic acid (20 ml) and heated at 100° C. for 20 minutes. After being cooled to room temperature, the mixture was concentrated to dryness. The residue was flushed with water and then with ethanol twice, and recrystallized from ethanol/ether to obtain methyl 1-α-O-benzyl-N-benzyloxyacetylmuramyl-L-valyl-D-isoglutaminate (359 mg). m.p. 180°–182° C. $[\alpha]_D^{23}$ +89.2° (C 0.5, DMF). $R_f^2 = 0.46$, $R_f^4 = 0.72$ Elemental analysis for $C_{36}H_{50}O_{12}N_4$: Calculated: C, 59.16; H, 6.90; N, 7.67. Found: C, 59.23; H, 7.11; N, 7.55.

(VIII) QS-10-OH p-nitrophenyl ester (142 mg, 0.3 mmol), methyl 1-α-O-benzyl-N-benzyloxyacetylmuramyl-L-valyl-D-isoglutaminate (109.2 mg, 0.15 mmol) and 1-hydroxybenzotriazole (hereinafter referred to as HOBt; 81 mg, 0.15 mmol) were dissolved together with NEM (0.077 ml) in DMF (0.8 ml) and the resulting solution was stirred at room temperature for 60 hours. After evaporation, the residue was purified by the column chromatography on silicagel (15 g) (column size 1.5×12 cm, elution solvent: chloroform/acetone/ethanol=70:30:3, v/v). The fractions containing the pure desired product were collected and the solvent was evaporated. The residue was freeze-dried from t-butanol to obtain methyl 1-α-O-benzyl-6-O-(QS-10)-N-benzyloxyacetylmuramyl-L-valyl-D-isoglutaminate (102 mg). The resulting ester was catalytically hydrogenated in methanol (10 ml) using palladium black as a catalyst. Sixteen hours later, the catalyst was filtered, and the solvent was evaporated. The residue was crystallized using methanol/ether and the crystals were filtered. The crystals were then dissolved in methanol (5 ml) and a solution of ferric chloride (0.5 mg) in water (0.5 ml) was added. After being stirred at room temperature for 30 minutes, the methanol was evaporated. Ethyl acetate (15 ml) and water (10 ml) were added to the resulting aqueous solution and extracted. The aqueous layer was further extracted with ethyl acetate (15 ml). The combined extract was washed, dried over anhydrous sodium sulfate and evaporated. The residue was purified by the column chromatography on Sephadex LH-20 (column size 1.5×90 cm, elution solvent: 0.1 N acetic acid/ethanol=2:3, v/v). The fractions containing the desired product (72 ml–88 ml) were collected and the solvent was evaporated. The crystalline residue was recrystallized from methanol/water to obtain methyl 6-O-(QS-10)-N-glycolymuramyl-L-valyl-D-isoglutaminate (39.3 mg). m.p. 217°–220° C. $[\alpha]_D^{22}$ +27.6° (C 0.5, ethanol). $R_f^1$=0.78, $R_f^2$=0.32, $R_f^4$=0.71.

Elemental analysis for $C_{41}H_{63}O_{17}N_4$: Calculated: C, 55.71; H, 7.18; N, 6.34. Found: C, 55.57; H, 7.23; N, 6.08.

EXAMPLE 6

(I) Benzyl t-butyloxycarbonyl-L-valyl-D-isoglutaminate (7.5 g, 17.2 mmol) was catalytically hydrogenated in methanol (150 ml) using palladium black as a catalyst at room temperature for 6 hours. The catalyst was filtered and the solvent was evaporated. Petroleum ether was added to the residue. After trituration, the resulting powder was filtered. Reprecipitation from ethyl acetate/petroleum ether gave t-butyloxycarbonyl-L-valyl-D-isoglutamine (6.0 g). m.p. 89°–90° C. (dec.). $[\alpha]_D^{23}$ +9.46° (C 0.5, DMF). $R_f^2$=0.32.

(II) To a solution of t-butyloxycarbonyl-L-valyl-D-isoglutamine (1.73 g, 5 mmol) in DMF (5 ml) was added TEA (0.84 ml) and 6-chloro-1-p-chlorobenzenesulfonyloxybenzotriazole (2.06 g, 6 mmol) under cooling. After being stirred at room temperature for 4 hours, the mixture was cooled with ice again and ethanol (3 ml) and TEA (0.7 ml) were added. The mixture was stirred at room temperature for 24 hours. Ethyl acetate (100 ml) was added to the reaction mixture and the organic layer was then washed with a 5% aqueous sodium bicarbonate solution, 1 N hydrochloric acid and water successively. The mixture was then dried over anhydrous sodium sulfate and evaporated. The crystalline residue was recrystallized from ethyl acetate/petroleum ether to obtain ethyl t-butyloxycarbonyl-L-valyl-D-isoglutaminate (820 mg). m.p. 128°–129° C. $[\alpha]_D^{23}$ +8.4° (C 0.5, DMF). $R_f^2$=0.72, $R_f^3$=0.28.

Elemental analysis for $C_{17}H_{31}O_6N_3$: Calculated: C, 54.67; H, 8.37; N, 11.25. Found: C, 54.71; H, 8.21; N, 11.31.

(III) A solution of ethyl t-butyloxycarbonyl-L-valyl-D-isoglutaminate (747 mg, 2 mmol) in trifluoroacetic acid (5 ml) was allowed to stand at room temperature for 20 minutes. After evaporation, ether was added to the residue and the resulting powder was filtered. This trifluoroacetic acid salt was dissolved in acetonitrile (5 ml) and neutralized with TEA (0.28 ml). Then, 1-α-O-benzyl-4,6-O-benzylidene-N-acetylmuramic acid HONB ester (1.26 g, 2 mmol) was added and the mixture was allowed to react at room temperature for 15 hours. The resulting crystals were filtered and washed with acetonitrile to obtain ethyl 1-α-O-benzyl-4,6-O-benzylidene-N-acetylmuramyl-L-valyl-D-isoglutaminate (1.08 g). m.p.>255° C. $[\alpha]_D^{23}$ +98.4° (C 0.5, DMF), $R_f^2$=0.69, $R_f^4$=0.72.

Elemental analysis for $C_{37}H_{50}O_{11}N_4$: Calculated: C, 61.14; H, 6.93; N, 7.71. Found: C, 61.00; H, 6.97; N, 7.65.

(IV) Ethyl 1-α-O-benzyl-4,6-O-benzylidene-N-acetylmuramyl-L-valyl-D-isoglutaminate (1.00 g, 1.37 mmol) was dissolved in 75% acetic acid (20 ml) and heated at 100° C. for 20 minutes. The reaction mixture was allowed to cool to room temperature, evaporated, and flushed with water and then with toluene twice. The crystalline residue was recrystallized from ethanol/ether to obtain ethyl 1-α-O-benzyl-N-acetylmuramyl-L-valyl-D-isoglutaminate (837 mg). m.p. 235° C. $[\alpha]_D^{23}$ +110.5° (C 0.5, DMF). $R_f^2$=0.35, $R_f^4$=0.35.

Elemental analysis for $C_{30}H_{46}O_{11}N_4$: Calculated: C, 56.41; H, 7.26; N, 8.77. Found: C, 56.04; H, 7.22; N, 8.61.

(V) QS-10-OH p-nitrophenyl ester (142 mg, 0.3 mmol), ethyl 1-α-O-benzyl-N-acetylmuramyl-L-valyl-D-isoglutaminate (95.8 mg, 0.15 mmol) and $HOB_t$ (81 mg, 0.6 mmol) were dissolved together with NEM (0.077 ml) in DMF (0.7 ml) and the mixture was stirred at room temperature for 4 days. After evaporation the residue was purified by the column chromatography on silica gel (column size 1.5×12 cm, elution solvent:methanol/chloroform=5:95, v/v). The fractions containing the pure desired product were collected and the solvent was evaporated. The residue was crystallized from ethanol/ether to obtain ethyl 1-α-O-benzyl-6-O-(QS-10)-N-acetylmuramyl-L-valyl-D-isoglutaminate (60 mg). m.p. 177° C. $[\alpha]_D^{23}$ +66.7° (C 0.5, chloroform). $R_f^2$=0.75, $R_f^3$=0.17, $R_f^4$=0.68.

Elemental analysis for $C_{49}H_{72}O_{16}N_4 \cdot \frac{1}{2}H_2O$: Calculated: C, 59.92; H, 7.49; N, 5.71. Found: C, 59.73; H, 7.32; N, 5.85.

EXAMPLE 7

Ethyl 1-α-O-benzyl-6-O-(QS-10)-N-acetylmuramyl-L-valyl-D-isoglutaminate (55 mg) was catalytically hydrogenated in ethanol (5 ml) using palladium black as a catalyst at room temperature for 4 hours. The catalyst was removed by the filtration and the solvent was evaporated. The residue was dissolved in ethanol (5 ml) and a solution of ferric chloride (0.5 mg) in water (0.5 ml) was added. The reaction mixture was then stirred at room temperature for 30 minutes. After evaporation, the residue was extracted with a mixture of ethyl acetate (15 ml) and water (3 ml). The ethyl acetate layer was washed with water, dried over anhydrous sodium sulfate and evaporated. The residue was purified by the column chromatography on Sephadex LH-20 (column size 1.5×90 cm, elution solvent:ethanol). The fractions containing the pure desired product were collected and the solvent was evaporated. The residue was freeze-dried from t-butanol to obtain ethyl 6-O-(QS-10)-N-acetylmuramyl-L-valyl-D-isoglutaminate (41 mg).

[α]$_D^{23}$ +33.0° (C 0.5, ethanol). R$_f^1$=0.84, R$_f^2$=0.36, R$_f^4$=0.73

Elemental analysis for C$_{42}$H$_{66}$O$_{16}$N$_4$.H$_2$O: Calculated: C, 55.98; H, 7.61; N, 6.22. Found: C, 55.67; H, 7.53; N, 6.07.

EXAMPLE 8

(I) t-Butyloxycarbonyl-L-valyl-D-isoglutamine (1.73 g, 5 mmol) and 6-chloro-1-p-chlorobenzenesulfonyloxybenzotriazole (2.06 g, 6 mmol) were reacted in DMF (5 ml) in the presence of TEA (0.84 ml) in a similar manner to that in Example 6 (II). Then stearyl alcohol (4.05 g, 15 mmol) and TEA (0.7 ml) were added and the mixture was reacted at room temperature for 20 hours. The usual work-up as described in Example 6 (II) gave stearyl t-butyloxycarbonyl-L-valyl-D-isoglutaminate (1.10 g). m.p. 88°-89° C. [α]$_D^{23}$ +4.0° (C 0.5, DMF). R$_f^2$=0.68, R$_f^3$=0.34

Elemental analysis for C$_{33}$H$_{63}$O$_6$N$_3$: Calculated: C, 66.29; H, 10.62; N, 7.03. Found: C, 66.26; H, 11.10; N, 7.10.

(II) Stearyl 1-α-O-benzyl-4,6-O-benzylidene-N-acetylmuramyl-L-valyl-D-isoglutaminate (1.21 g) was obtained from stearyl t-butyloxycarbonyl-L-valyl-D-isoglutaminate (896.8 mg, 1.5 mmol) and 1-α-O-benzyl-4,6-O-benzylidene-N-acetylmuramic acid HONB ester (948 mg, 1.5 mmol) as described in Example 6 (III). m.p. 249° C. (dec.). [α]$_D^{23}$ +67.5° (C 0.5, DMF). R$_f^2$=0.70, R$_f^4$=0.85.

Elemental analysis for C$_{53}$H$_{82}$O$_{11}$N$_4$.H$_2$O: Calculated: C, 65.67; H, 8.74; N, 5.78. Found: C, 65.81; H, 8.66; N, 5.90.

(III) Stearyl 1-α-O-benzyl-N-acetylmuramyl-L-valyl-D-isoglutaminate (832 mg) was obtained from stearyl 1-α-O-benzyl-4,6-O-benzylidene-N-acetylmuramyl-L-valyl-D-isoglutaminate (1.16 g, 1.15 mmol) as described in Example 6 (IV). m.p. 231° C. [α]$_D^{23}$ +85.1° (C 0.5, DMF). R$_f^2$=0.49, R$_f^4$=0.49

Elemental analysis for C$_{46}$H$_{78}$O$_{11}$N$_4$: Calculated: C, 64.01; H, 9.11; n, 6.49. Found: C, 63.94; H, 9.19; N, 6.47.

(IV) Stearyl 1-α-O-benzyl-N-acetylmuramyl-L-valyl-D-isoglutaminate (130 mg, 0.15 mmol), QS-10-OH p-nitrophenyl ester (142 mg, 0.3 mmol) and HOBt (81 mg, 0.6 mmol) were dissolved together with NEM (0.078 ml) in DMF (1.5 ml) and the mixture was stirred at 60° C. for 48 hours. After evaporation, the residue was purified in a similar manner to that described in Example 6 (V) to obtain stearyl 1-α-O-benzyl-6-O-(QS-10)-N-acetylmuramyl-L-valyl-D-isoglutaminate (55 mg). m.p. 180° C. [α]$_D^{22}$ +38.3° (C 0.5, chloroform). R$_f^2$=0.74, R$_f^3$=0.22, R$_f^4$=0.85

Elemental analysis for C$_{65}$H$_{104}$O$_{16}$N$_4$.H$_2$O: Calculated: C, 64.22; H, 8.79; N, 4.61. Found: C, 64.22; H, 8.61; N, 5.21.

EXAMPLE 9

Stearyl 1-α-O-benzyl-6-O-(QS-10)-N-acetylmuramyl-L-valyl-D-isoglutaminate (48 mg, 0.04 mmol) was catalytically hydrogenated in dioxane (15 ml) using palladium black as a catalyst at room temperature for 6 hours. After filtration and evaporation, the residue was dissolved again in dioxane (15 ml). To this was added a solution of ferric chloride (0.5 g) in water (0.5 ml) and the mixture was stirred at room temperature for 30 minutes. After evaporation, chloroform (20 ml) and water (3 ml) were added to the residue and extracted. The chloroform layer was washed with water, dried over anhydrous sodium sulfate and evaporated. The residue was purified by the column chromatography on Sephadex LH-20 (column size 1.8×45 cm; elution solvent : chloroform). The fractions containing the pure desired product were collected and the solvent was evaporated. The residue was freeze-dried from t-butanol to obtain stearyl 6-O-(QS-10)-N-acetylmuramyl-L-valyl-D-isoglutaminate (17 mg). [α]$_D^{23}$ +20.3° (C 0.5, chloroform). R$_f^1$=0.81, R$_f^2$=0.54.

Elemental analysis for C$_{58}$H$_{100}$O$_{16}$N$_4$.½H$_2$O: Calculated: C, 62.28; H, 9.10; N, 5.01. Found: C, 62.23; H, 8.93; N, 5.18.

EXAMPLE 10

(I) Ethyleneglycol monomethylether (10 ml) was cooled to −60° C. and thionyl chloride (1 ml, 14 mmol) was added. Then D-glutamic acid (1.5 g, 10 mmol) was added and the mixture was reacted at room temperature for 2 hours. Ether (200 ml) was added. The precipitated oily material was washed thoroughly with ether and dryed in a desiccator over sodium hydroxide pellets. The dried product was crystallized from dioxane/ether to obtain D-glutamic acid γ-methoxyethyl ester hydrochloride (1.2 g, m.p. 174° C.). The resulting hydrochloride was dissolved together with S-t-butyloxycarbonyl-4,6-dimethyl-2-mercaptopyrimidine (1.79 g, 7.44 mmol) and TEA (1.38 ml) in a mixture of water (5 ml) and DMF (5 ml) and the mixture was stirred at room temperature for 20 hours. Water (20 ml) and ether (20 ml) were added to the reaction mixture and the excess S-t-butyloxycarbonyl-4,6-dimethyl-2-mercaptopyridine was extracted. The aqueous layer was, after being cooled, acidified to pH 2 with 2 N hydrochloric acid. The aqueous layer was then extracted with ethyl acetate (20 ml, twice). The combined ethyl acetate layer was washed with water, dried over anhydrous sodium sulfate and evaporated. The residue was dissolved in ether (20 ml) and dicyclohexylamine (0.91 ml) was added. The mixture was cooled. The crystals were filtered to obtain t-butyloxycarbonyl-D-glutamic acid γ-2-methoxyethyl ester dicyclohexylamine salt (1.76 g). m.p. 123° C. [α]$_D^{23}$ −9.35° (C 0.5, DMF). R$_f^2$=0.75.

Elemental analysis for C$_{25}$H$_{46}$O$_7$N$_2$: Calculated: C, 61.70; H, 9.53; N, 5.76. Found: C, 61.77; H, 9.62; N, 5.93.

(II) t-Butyloxycarbonyl-D-glutamic acid γ-2-methoxyethyl ester dicyclohexylamine salt (730 mg, 1.5 mmol) was suspended in ethyl acetate (20 ml). This suspension was shaken with 1 N sulfuric acid. The organic layer was washed with water, dried over anhydrous sodium sulfate and evaporated. The residue was dissolved together with N-hydroxysuccinimide (190 mg, 1.65 mmol) in acetonitrile (10 ml). To this was added, DCC (340 mg, 1.65 mmol) under ice-cooling and the mixture was reacted under ice cooling for one hour and then at room temperature for 15 hours. The insoluble material was filtered. To the filtrate was added concentrated ammonia water (0.6 ml), the mixture was stirred for 30 minutes. After evaporation, the residue was purified by the column chromatography on silica gel (column size 2.5×15 cm; elution solvent:methanol:chloroform=5:95, v/v). The fractions containing the desired product were collected and the solvent was evaporated. The residue was triturated with petroleum ether and the resulting crystals were filtered to obtain 2-methoxyethyl t-butyloxycarbonyl-D-isoglutaminate (346 mg). m.p. 108°-109° C. [α]$_D^{23}$ −4.73° (C 0.5, DMF). R$_f^2$=0.62, R$_f^3$=0.27.

Elemental analysis for $C_{13}H_{24}O_6N_2$: Calculated: C, 51.30; H, 7.95; N, 9.21. Found: C, 51.15; H, 7.99; N, 9.11.

(III) 2-Methoxyethyl t-butyloxycarbonyl-D-isoglutaminate (183 mg, 0.6 mmol) was treated with trifluoroacetic acid (2 ml) as described in Example 5 (V). The resulting trifluoroacetic acid salt was dissolved in acetonitrile (5 ml) and neutralized with TEA (0.1 ml). To this was added t-butyloxycarbonyl-L-valine HONB ester (277 mg, 0.6 mmol) and the mixture was stirred at room temperature for 15 hours. The purification similar to that described in Example 5 (V) gave 2-methoxyethyl t-butyloxycarbonyl-L-valyl-D-isoglutaminate (180 mg). m.p. 107°–108° C. $[\alpha]_D^{22}$ +8.77° (C 0.5, DMF). $R_f^2=0.76$, $R_f^3=0.29$ Elemental analysis for $C_{18}H_{33}O_7N_3$: Calculated: C, 53.58; H, 8.24; N, 10.41. Found: C, 53.81; H, 8.39; N, 10.28.

(IV) 2-Methoxyethyl t-butyloxycarbonyl-L-valyl-D-isoglutaminate (160 mg, 0.4 mmol) was treated with trifluoroacetic acid (2 ml) as described in Example 6 (III). The resulting trifluoroacetic acid salt was reacted with 1-α-O-benzyl-4,6-O-benzylidene-N-acetylmuramic acid HONB ester (253 mg, 0.4 mmol) in acetonitrile (10 ml) in the presence of TEA (0.06 ml). The purification in a similar manner to that described in Example 6 (III) gave 2-methoxyethyl 1-α-O-benzyl-4,6-O-benzylidene-N-acetylmuramyl-L-valyl-D-isoglutaminate (263 mg). m.p.>240° C. $[\alpha]_D^{22}$ +91.7° (C 0.5, DMF). $R_f^2=0.72$, $R_f^4=0.75$.

Elemental analysis for $C_{38}H_{52}O_{12}N_4$: Calculated: C, 60.31; H, 6.93; N, 7.40. Found: C, 60.39; H, 6.99; N, 7.32.

(V) 2-Methoxyethyl 1-α-O-benzyl-4,6-O-benzylidene-N-acetylmuramyl-L-valyl-D-isoglutaminate (243 mg, 0.32 mmol) was reacted in 75% acetic acid (20 ml). The mixture was then subjected to the work-up similar to that described in Example 6 (IV) to obtain 2-methoxyethyl 1-α-O-benzyl-N-acetylmuramyl-L-valyl-D-isoglutaminate (183 mg). m.p. 198°–200° C. $[\alpha]_D^{22}$ +106.7° (C 0.5, DMF). $R_f^2=0.26$, $R_f^4=0.69$.

Elemental analysis for $C_{31}H_{48}O_{12}N_4 \cdot \frac{1}{2}H_2O$: Calculated: C, 54.93; H, 7.29; N, 8.27. Found: C, 54.75; H, 7.28; N, 8.19.

(VI) 2-Methoxyethyl 1-α-O-benzyl-N-acetylmuramyl-L-valyl-D-isoglutaminate (100.3 mg, 0.15 mmol), QS-10-OH p-nitrophenyl ester (142 mg, 0.3 mmol) and HOBt (81 mg, 0.6 mmol) were dissolved together with NEM (0.078 ml) in DMF (0.8 ml) and the mixture was stirred at room temperature for 60 hours. The purification similar to that in Example 6 (V) gave 2-methoxyethyl 1-α-O-benzyl-6-O-(QS-10)-N-acetylmuramyl-L-valyl-D-isoglutaminate (54 mg). $[\alpha]_D^{22}$ +70.7° (C 0.5, ethanol). $R_f^2=0.69$, $R_f^3=0.18$, $R_f=0.18$ (chloroform:acetone:ethanol=70:30:3, v/v; silica gel plate; the $R_f$ value obtained under these conditions is hereinafter referred to as $R_f^5$).

Elemental analysis for $C_{50}H_{74}O_{17}N_4$: Calculated: C, 59.86; H, 7.44; N, 5.59. Found: C, 60.19; H, 7.55; N, 5.61.

EXAMPLE 11

2-Methoxyethyl 1-α-O-benzyl-6-O-(QS-10)-N-acetylmuramyl-L-valyl-D-isoglutaminate (40 mg, 0.04 mmol) was catalytically hydrogenated in methanol (5 ml) using palladium black as a catalyst at room temperature for 8 hours. After filtration and evaporation, the product was dissolved in methanol (5 ml). To this was added a solution of ferric chloride (400 mg) in water (0.5 ml) and the reaction mixture was stirred at room temperature for 30 minutes. The purification similar to that described in Example 7 gave 2-methoxyethyl 6-O-(QS-10)-N-acetylmuramyl-L-valyl-D-isoglutaminate (30 mg). m.p. 193°–195° C. $[\alpha]_D^{22}$ +40.7° (C 0.5, ethanol). $R_f^1=0.83$, $R_f^2=0.38$, $R_f^4=0.70$.

Elemental analysis for $C_{43}H_{68}O_{17}N_4 \cdot \frac{1}{2}H_2O$: Calculated: C, 56.01; H, 7.11; N, 6.08. Found: C, 56.09; H, 7.56; N, 6.00.

EXAMPLE 12

(I) t-Butyloxycarbonyl-L-valyl-D-isoglutamine (1.05 g, 3.04 mmol) and 6-chloro-1-p-chlorobenzenesulfonyloxybenzotriazole (1.24 g, 3.6 mmol) were reacted in DMF (5 ml) in the presence of TEA (0.5 ml) according to the procedure described in Example 6 (II). To the resulting mixture was added n-hexanol (3 ml) and TEA (0.5 ml). The mixture was then stirred at room temperature for 2 hours. The purification similar to that described in Example 6 (II) gave n-hexyl t-butyloxycarbonyl-L-valyl-D-isoglutaminate (287 mg). m.p. 94°–95° C. $[\alpha]_D^{22}$ +9.41° (C 0.5, DMF). $R_f^2=0.71$, $R_f^3=0.34$ Elemental analysis for $C_{21}H_{39}O_6N_3 \cdot \frac{1}{2}H_2O$: Calculated: C, 57.51; H, 9.19; N, 9.58. Found: C, 57.66; H, 8.92; N, 9.96.

(II) n-Hexyl t-butyloxycarbonyl-L-valyl-D-isoglutaminate (267 mg, 0.62 mmol) was treated with trifluoroacetic acid (2 ml) at room temperature for 20 minutes and worked-up as described in Example 6 (III). The resulting trifluoroacetic acid salt was dissolved in acetonitrile (25 ml). To this solution was added TEA (0.1 ml) and 1-α-O-benzyl-4,6-O-benzylidene-N-acetylmuramic acid HONB ester (392 mg, 0.62 mmol) and the mixture was stirred at room temperature for 15 hours. The purification similar to that described in Example 6 (III) gave n-hexyl 1-α-O-benzyl-4,6-O-benzylidene-N-acetylmuramyl-L-valyl-D-isoglutaminate (370 mg). m.p. 240° C. $[\alpha]_D^{22}$ +93.4° (C 0.5, DMF). $R_f^2=0.60$, $R_f^4=0.86$.

Elemental analysis for $C_{41}H_{58}O_{11}N_4$: Calculated: C, 62.90; H, 7.47; N, 7.16. Found: C, 62.74; H, 7.33; N, 7.23.

(III) n-Hexyl 1-O-benzyl-4,6-O-benzylidene-N-acetylmuramyl-L-valyl-D-isoglutaminate (320 mg, 0.41 mmol) was dissolved in 75% acetic acid (20 ml) and heated at 100° C. for 20 minutes. The purification similar to that described in Example 6 (IV) gave n-hexyl 1-α-O-benzyl-N-acetylmuramyl-L-valyl-D-isoglutaminate (223 mg). m.p. 210°–212° C. $[\alpha]_D^{22}$ +101.6° (C 0.5, DMF). $R_f^2=0.30$, $R_f^4=0.70$.

Elemental analysis for $C_{34}H_{54}O_{11}N_4 \cdot \frac{1}{2}H_2O$: Calculated: C, 58.02; H, 7.88; N, 7.96. Found: C, 57.99; H, 7.91; N, 7.95.

(IV) n-Hexyl 1-α-O-benzyl-N-acetylmuramyl-L-valyl-D-isoglutaminate (104 mg, 0.15 mmol), QS-10-OH p-nitrophenyl ester (142 mg, 0.3 mmol) and HOBt (81 mg, 0.6 mmol) were dissolved together with NEM (0.077 ml) in DMF (0.8 ml) and the mixture was stirred at room temperature for 60 hours. The purification similar to that described in Example 6

(V) gave n-hexyl 1-α-O-benzyl-6-O-(QS-10)-N-acetylmuramyl-L-valyl-D-isoglutaminate (58 mg). m.p. 174°–176° C. $[\alpha]_D^{22}$ +46.9° (C 0.5, chloroform). $R_f^2=0.78$, $R_f^3=0.18$, $R_f^5=0.17$.

Elemental analysis for $C_{53}H_{80}O_{16}N_4$: Calculated: C, 61.85; H, 7.84; N, 5.44. Found: C, 61.75; H, 7.74; N, 5.37.

EXAMPLE 13 n-Hexyl 1-α-O-benzyl-6-O-(QS-10)-N-acetylmuramyl-L-valyl-D-isoglutaminate (54 mg, 0.052 mmol) was catalytically hydrogenated in methanol (5 ml) using palladium black as a catalyst at room temperature for 2 hours. The catalyst was removed and the solvent was evaporated. Oxidation of the resulting product with ferric chloride (500 mg) and the work-up as described in Example 7 gave n-hexyl 6-O-(QS-10)-N-acetylmuramyl-L-valyl-D-isoglutaminate (28 mg). m.p. 200°–202° C. $[\alpha]_D^{22}$ +39.2° (C 0.5, ethanol). $R_f^1=0.87$, $R_f^2 0.57$, $R_f^4=0.65$.

Elemental analysis for $C_{46}H_{74}O_{16}N_4 \cdot H_2O$: Calculated: C, 57.72; H, 8.00; N, 5.85. Found: C, 57.59; H, 7.91; N, 6.06.

EXAMPLE 14

(I) A mixture of benzyloxycarbonyl-D-isoglutamic acid (4.0 g, 14.2 mmol), paraformaldehyde (0.5 g) and p-toluenesulfonic acid (0.14 g) in benzene (200 ml) was heated under reflux for 8 hours. The water formed was removed azeotropically. The mixture was then washed with water, dried over anhydrous sodium sulfate and evaporated. The oily residue was dissolved in dichloromethane (30 ml) and concentrated sulfuric acid (0.15 ml) was added. Isobutene was saturated in the solution and, with sealing, reacted at room temperature for 4 days. Sodium bicarbonate (0.5 g) was added and the solvent was evaporated. The residue was dissolved in ethyl acetate (50 ml), washed with a 5% aqueous sodium bicarbonate solution, a 10% citric acid and water successively, dried over anhydrous sodium sulfate and evaporated. The resulting residue was dissolved in ethanol (20 ml) and 1 N aqueous sodium hydroxide solution (13.6 ml) was added dropwise to this solution under cooling. The mixture was then stirred at room temperature for one hour. After evaporation of ethanol, water (20 ml) and ethyl acetate (20 ml) were added to the residual aqueous solution. After extraction, the aqueous layer was cooled and its pH was adjusted to 2 by adding 1 N hydrochloric acid. The aqueous layer was extracted with ethyl acetate which was washed with water, dried over anhydrous sodium sulfate and evaporated. The residue was dissolved in ether (20 ml) and dicyclohexylamine (1.77 ml) was added. After cooling, the crystals were filtered to obtain benzyloxycarbonyl-D-glutamic acid γ-t-butyl ester dicyclohexylammonium salt (3.03 g). m.p. 139°–140° C. $[\alpha]_D^{22}$ +7.0° (C 0.5, methanol). $R_f^2=0.69$.

(II) Benzyloxycarbonyl-D-glutamic acid γ-t-butyl ester dicyclohexylammonium salt (778 mg, 1.5 mmol) was suspended in ethyl acetate (20 ml) and 1 N sulfuric acid was added. After extraction, the ethyl acetate layer was washed with water, dried over anhydrous sodium sulfate and evaporated. The resulting oily material was dissolved together with N-hydroxysuccinimide (207 mg, 1.8 mmol) in acetonitrile (10 ml). To this was added DCC (371 mg, 1.8 mmol) under cooling and the mixture was stirred under ice-cooling for 30 minutes and at room temperature for 2 hours. The reaction mixture was filtered to remove the precipitate and the filtrate was cooled. Ammonia water (0.6 ml) was then added and the mixture was stirred under ice cooling for 30 minutes. After evaporation, the crystalline residue was washed with hot water to obtain t-butyl benzyloxycarbonyl-D-isoglutaminate (342 mg). m.p. 133° C. $[\alpha]_D^{22}$ −2.5° (C 0.5, DMF). $R_f^2=0.79$, $R_f^3=0.42$ Elemental analysis for $C_{17}H_{24}O_5N_2$: Calculated: C, 60.70; H, 7.19; N, 8.33. Found: C, 61.13; H, 7.23; N, 8.36.

(III) t-Butyl benzyloxycarbonyl-D-isoglutaminate (202 mg, 0.6 mmol) was catalytically hydrogenated in methanol (10 ml) using palladium black as a catalyst at room temperature for 3 hours. The catalyst was removed by the filtration and the solvent was evaporated. The residue was dissolved in acetonitrile (10 ml) and benzyloxycarbonyl-L-valine HONB ester (245 mg, 0.6 mmol) was added. After being stirred at room temperature for 15 hours, the reaction mixture was evaporated. A 5% citric acid aqueous solution (30 ml) was added to the residue and the mixture was cooled. The resulting crystals were filtered, washed with water and recrystallized from ethyl acetate/petroleum ether to obtain t-butyl benzyloxycarbonyl-L-valyl-D-isoglutaminate (178 mg). m.p. 210°–211° C. $[\alpha]_D^{22}$ +19.1° (C 0.5, DMF). $R_f^2=0.68$, $R_f^3=0.35$.

Elemental analysis for $C_{22}H_{33}O_6N_3$: Calculated: C, 60.67; H, 7.64; N, 9.65. Found: C, 60.51; H, 7.56; N, 9.60.

(IV) t-Butyl benzyloxycarbonyl-L-valyl-D-isoglutaminate (160 mg, 0.38 mmol) was catalytically hydrogenated in methanol (20 ml) using palladium black as a catalyst at room temperature for 2 hours. After filtration and evaporation, the residue was dissolved in acetonitrile (6 ml), and 1-α-O-benzyl-4,6-O-benzylidene-N-acetylmuramic acid HONB ester (240.4 mg, 0.38 mmol) was added. The mixture was then stirred at room temperature for 15 hours. After the addition of ether (30 ml), the mixture was cooled and the resulting crystals were collected and recrystallized from acetonitrile/ether to obtain t-butyl 1-α-O-benzyl-4,6-O-benzylidene-N-acetylmuramyl-L-valyl-D-isoglutaminate (216 mg). m.p. 186°–188° C. (dec.). $[\alpha]_D^{22}$ +97.4° (C 0.5, DMF). $R_f^2=0.76$, $R_f^4=0.71$.

Elemental analysis for $C_{39}H_{54}O_{11}N_4$: Calculated: C, 61.92; H, 7.21; N, 7.42. Found: C, 62.20; H, 7.25; N, 7.56.

(V) t-Butyl 1-α-O-benzyl-4,6-O-benzylidene-N-acetylmuramyl-L-valyl-D-isoglutaminate (196 mg, 0.26 mmol) was heated in 60% acetic acid (20 ml) at 100° C. for 15 minutes. The purification similar to that described in Example 6 (IV) gave t-butyl 1-α-O-benzyl-N-acetylmuramyl-L-valyl-D-isoglutaminate (120 mg). m.p. 197°–199° C. $[\alpha]_D^{21}$ +110.3° (C 0.5, DMF). $R_f^2=0.39$ Elemental analysis for $C_{32}H_{50}O_{11}N_4 \cdot \frac{1}{2}H_2O$: Calculated: C, 56.84; H, 7.60; N, 8.27. Found: C, 56.84; H, 7.55; N, 8.19.

(VI) t-Butyl 1-α-O-benzyl-N-acetylmuramyl-L-valyl-D-isoglutaminate (100.6 mg, 0.15 mmol), QS-10-OH p-nitrophenyl ester (142 mg, 0.3 mmol) and HOBt (81 mg, 0.6 mmol) were dissolved together with NEM (0.077 ml) in DMF (0.8 ml) and the mixture was stirred at room temperature for 80 hours. The purification was conducted in a similar manner to that described in Example 6 (V) to obtain t-butyl 1-α-O-benzyl-6-O-(QS-10)-N-acetylmuramyl-L-valyl-D-isoglutaminate (80 mg). m.p. 157° C. $[\alpha]_D^{22}$ +65.6° (C 0.5, ethanol). $R_f^2=0.74$, $R_f^3=0.30$, $R_f^4=0.70$, $R_f^5=0.20$.

Elemental analysis for $C_{51}H_{76}O_{10}N_4$: Calculated: C, 61.18; H, 7.65; N, 5.60. Found: C, 61.16; H, 7.65; N, 5.61.

EXAMPLE 15 t-Butyl 1-α-O-benzyl-6-O-(QS-10)-N-acetylmuramyl-L-valyl-D-isoglutaminate (73 mg, 0.073 mmol) was catalytically hydrogenated in methanol (5 ml) using palladium black as a catalyst at room temperature for 7 hours. The catalyst was removed by the filtration and the solvent was distilled off. The residue was oxidized with ferric chloride (500 mg) and then worked-up according to the procedures described in Example 7 to obtain t-butyl 6-O-(QS-10)-N-acetylmuramyl-L-valyl-D-isoglutaminate (45 mg). m.p. 192°–193° C. $[\alpha]_D^{21}$ +35.6° (C 0.5, methanol). $R_f^1=0.87$, $R_f^2=0.54$, $R_f^4=0.59$.

Elemental analysis for $C_{44}H_{70}O_{16}N_4$: Calculated: C, 58.00; H, 7.75; N, 6.15. Found: C, 57.73; H, 7.83; N, 6.16.

EXAMPLE 16

(I) Isopropanol (40 ml) was cooled to −10° C. and thionyl chloride (2 ml, 27 mmol) was added dropwise, followed by the addition of D-glutamic acid (3 g, 20 mmol). The reaction was continued at room temperature for three days and the undissolved material was filtered. Ether (200 ml) was added to the filtrate liquor and cooled. The resulting crystals were collected to obtain D-glutamic acid γ-isopropyl ester (1.6 g). This ester was dissolved in a mixture of water (5 ml) and DMF (8 ml). To this solution was added TEA (1.84 ml) and s-t-butyloxycarbonyl-4,6-dimethyl-2-mercaptopyrimidine (1.91 g, 7.97 mmol) and the mixture was stirred at room temperature for 20 hours. The purification similar to that described in Example 10 (I) gave t-butyloxycarbonyl-D-glutamic acid γ-isopropyl ester dicyclohexylamine salt (2.5 g). m.p. 131° C. $[\alpha]_D^{23}$ −7.1° (C 0.5, DMF). $R_f^2=0.64$.

Elemental analysis for $C_{25}H_{46}O_6N_2$: Calculated: C, 63.80; H, 9.85; N, 5.95. Found: C, 63.57; H, 10.01; N, 6.08.

(II) t-Butyloxycarbonyl-D-glutamic acid γ-isopropyl ester dicyclohexylamine salt (2.4 g, 5.1 mmol) was suspended in ethyl acetate (20 ml). The suspension was shaked with 1 N sulfuric acid and the ethyl acetate layer was washed with water, dried over anhydrous sodium sulfate and evaporated. The resulting oily residue was dissolved in acetonitrile (10 ml) and N-hydroxysuccinimide (0.65 g, 5.6 mmol) was added. Then, DCC (1.14 g, 5.6 mmol) was added under ice-cooling and the mixture was stirred under ice-cooling for one hour and at room temperature for 15 hours. After filtration and evaporation, petroleum ether was added to the crystalline residue. The crystals were filtered to obtain t-butyloxycarbonyl-γ-O-isopropyl-D-glutamic acid N-hydroxysuccinimide ester (1.45 g). m.p. 140°-142° C. $R_f^2=0.79$, $R_f^3=0.63$.

Elemental analysis for $C_{17}H_{26}O_8N_2$: Calculated: C, 52.84; H, 6.78; N, 7.25. Found: C, 52.81; H, 6.76; N, 7.42.

(III) t-Butyloxycarbonyl-γ-O-isopropyl-D-glutamic acid N-hydroxysuccinimide ester (580 mg, 1.5 mmol) was dissolved in dioxane (6 ml). To this was added ammonia water (0.6 ml) under ice-cooling and the reaction mixture was stirred under ice-cooling for 30 minutes and then at room temperature for 30 minutes. After evaporation, the crystalline residue was washed with hot water and recrystallized from ethyl acetate/petroleum ether to obtain isopropyl t-butyloxycarbonyl-D-isoglutaminate (375 mg). m.p. 148°-150° C. $[\alpha]_D^{23}$ −3.19° (C 0.5, DMF), $R_f^2=0.74$, $R_f^3=0.35$.

Elemental analysis for $C_{13}H_{24}O_5N_2$: Calculated: C, 54.15; H, 8.39; N, 9.72. Found: C, 54.00; H, 8.75; N, 9.63.

(IV) iso-Propyl t-butyloxycarbonyl-D-isoglutaminate (173 mg, 0.6 mmol) was dissolved in trifluoroacetic acid (2 ml) and the mixture was kept at room temperature for 20 minutes. After evaporation, the oily residue was washed with a mixture solvent of ether and petroleum ether (1:1, v/v) and dryed in a desiccator over sodium hydroxide pellets. The resulting trifluoroacetic acid salt was dissolved in acetonitrile (5 ml) and neutralized with triethylamine (0.1 ml). To this solution was added t-butyloxycarbonyl-L-valine HONB ester (277 mg, 0.6 mmol) and the reaction mixture was stirred at room temperature for 15 hours. After evaporation, the residue was extracted with ethyl acetate (20 ml). The extract was washed with a 5% aqueous sodium bicarbonate solution, 1 N hydrochloric acid and water successively, dried over anhydrous sodium sulfate, and evaporated. Petroleum ether was then added to the residue, after being cooled, the resulting crystals were collected to obtain iso-propyl t-butyloxycarbonyl-L-valyl-D-isoglutaminate (185 mg). m.p. 144°-145° C. $[\alpha]_D^{22}$ +10.2° (C 0.5, DMF). $R_f^1=0.79$, $R_f^3=0.33$.

Elemental analysis for $C_{18}H_{33}O_6N_3$: Calculated: C, 55.79; H, 8.58; N, 10.84. Found: C, 55.73; H, 8.59; N, 10.60.

(V) iso-Propyl t-butyloxycarbonyl-L-valyl-D-isoglutaminate (165 mg, 0.43 mmol) was treated with trifluoroacetic acid (2 ml) and resulting trifluoroacetic acid salt was reacted with 1-α-O-benzyl-4,6-O-benzylidene-N-acetylmuramic acid HONB ester (272 mg, 0.43 mmol) in acetonitrile (10 ml) in the presence of TEA (0.07 ml) in a similar manner to that described in Example 6 (III). The purification similar to that in Example 6 (III) gave iso-propyl 1-α-O-benzyl-4,6-O-benzylidene-N-acetylmuramyl-L-valyl-D-isoglutaminate (275 mg). m.p. >240° C. $[\alpha]_D^{22}$ +93.9° (C 0.5, DMF), $R_f^2=0.73$, $R_f^4=0.88$.

Elemental analysis for $C_{38}H_{52}O_{11}N_4$: Calculated: C, 61.60; H, 7.08; N, 7.56. Found: C, 61.89; H, 7.27; N, 7.36.

(VI) iso-Propyl 1-α-O-benzyl-4,6-O-benzylidene-N-acetylmuramyl-L-valyl-D-isoglutaminate (255 mg, 0.34 mmol) was reacted in 75% acetic acid (20 ml). The mixture was then worked-up in a similar manner to that described in Example 6 (IV) to obtain iso-propyl 1-α-O-benzyl-N-acetylmuramyl-L-valyl-D-isoglutaminate (190 mg). m.p. 207°-208° C. $[\alpha]_D^{22}$ +111.2° (C 0.5, DMF). $R_f^2=0.31$, $R_f^4=0.76$.

Elemental analysis for $C_{31}H_{48}O_{11}N_4 \cdot \frac{1}{2}H_2O$: Calculated: C, 56.26; H, 7.31; N, 8.46. Found: C, 56.26; H, 7.46; N, 8.43.

(VII) iso-Propyl 1-α-O-benzyl-N-acetylmuramyl-L-valyl-D-isoglutaminate (98 mg, 0.15 mmol), QS-10-OH p-nitrophenyl ester (142 mg, 0.3 mmol) and HOBt (81 mg, 0.6 mmol) were dissolved together with NEM (0.078 ml) in DMF (0.8 ml) and the mixture was stirred at room temperature for 60 hours. The purification similar to that described in Example 6 (V) gave iso-propyl 1-α-O-benzyl-6-O-(QS-10)-N-acetylmuramyl-L-valyl-D-isoglutaminate (84 mg). m.p. 177°-179° C. $[\alpha]_D^{22}$ +69.0° (C 0.5, ethanol). $R_f^2=0.63$, $R_f^3=0.22$, $R_f^5=0.20$.

Elemental analysis for $C_{50}H_{74}O_{16}N_4$: Calculated: C, 60.83; H, 7.56; N, 5.68. Found: C, 60.89; H, 7.67; N, 5.76.

EXAMPLE 17 iso-Propyl 1-α-O-benzyl-6-O-(QS-10)-N-acetylmuramyl-L-valyl-D-isoglutaminate (70 mg, 0.07 mmol) was catalytically hydrogenated in methanol (5 ml) using palladium black as a catalyst at room temperature for 15 hours. The catalyst was removed by filtration and the solvent was evaporated. The residue was oxidized with ferric chloride (500 mg) and then worked up according to the procedures described in Example 7 to obtain iso-propyl 6-O-(QS-10)-N-acetylmuramyl-L-valyl-D-isoglutaminate (44 mg). m.p. 194°-195° C. $[\alpha]_D^{22}$ +35.4° (C 0.5, ethanol). $R_f^1=0.86$, $R_f^2=0.49$, $R_f^4=0.74$.

Elemental analysis for $C_{43}H_{68}O_{16}N_4$: Calculated: C, 57.57; H, 7.64; N, 6.25. Found: C, 57.39; H, 7.75; N, 6.14.

EXAMPLE 18

(I) Methyl t-butyloxycarbonyl-L-valyl-D-isoglutaminate (5.39 mg, 15 mmol) was treated with trifluoroacetic acid (30 ml) in a similar manner to that described in Example 6 (III). The resulting trifluoroacetic acid salt was dissolved in acetonitrile (50 ml) and neutralized with TEA (2.1 ml). To this was added 1-α-O-benzyl-4,6-O-benzylidene-N-acetylmuramic acid HONB ester (9.48 g, 15 mmol). The mixture was stirred and then worked-up in a similar manner to that described in Example 6 (III) to give methyl 1-α-O-benzyl-4,6-O-benzylidene-N-acetylmuramyl-L-valyl-D-isoglutaminate (11.15 g). m.p. 242° C. (dec.). $[\alpha]_D^{22}$ +86.1° (C 0.5, DMF). $R_f^2 = 0.80$, $R_f^4 = 0.69$.

Elemental analysis for $C_{36}H_{48}O_{11}N_4 \cdot H_2O$: Calculated: C, 59.16; H, 6.90; N, 7.68. Found: C, 59.85; H, 6.80; N, 7.70.

(II) Methyl-1-α-O-benzyl-4,6-O-benzylidene-N-acetylmuramyl-L-valyl-D-isoglutaminate (10.1 g, 14.1 mmol) was reacted in 75% acetic acid (200 ml). The reaction mixture was then work-up in a similar manner to that described in Example 6 (IV) to obtain methyl 1-α-O-benzyl-N-acetylmuranyl-L-valyl-D-isoglutaminate (7.0 g). m.p. 242° C. $[\alpha]_D^{23}$ +111.3° (C 0.5, DMF). $R_f^2 = 0.37$, $R_f^4 = 0.25$.

Elemental analysis for $C_{29}H_{44}O_{11}N_4$: Calculated: C, 55.76; H, 7.10; N, 8.70. Found: C, 55.59; H, 7.16; N, 8.97.

(III) Methyl-1-α-O-benzyl-N-acetylmuramyl-L-valyl-D-isoglutaminate (3.12 g, 5 mmol), benzyloxycarbonyl-L-leucine p-nitrophenyl ester (3.86 g, 10 mmol) and HOBt (2.70 g, 20 mmol) were dissolved together with NEM (2.56 ml) in DMF (50 ml) and the reaction mixture was stirred at room temperature for 60 hours. After evaporation, the residue was purified by the column chromatography on silica gel (column size: 4×15 cm; elution solvent: methanol/chloroform=5:95, v/v). The fractions containing the pure desired product were collected and the solvent was removed. Ether was added to the residue. The trituration gave powder which was reprecipitated from methanol/ether to obtain methyl 1-α-O-benzyl-6-O-(benzyloxycarbonyl-L-leucyl)-N-acetylmuramyl-L-valyl-D-isoglutaminate (3.1 g). m.p. 232°–234° C. $[\alpha]_D^{22}$ +72.2° (C 0.5, DMF). $R_f^2 = 0.65$, $R_f^3 = 0.10$, $R_f^4 = 0.60$.

Elemental analysis for $C_{43}H_{61}O_{14}N_5$: Calculated: C, 59.23; H, 7.05; N, 8.03. Found: C, 58.98; H, 7.19; N, 8.10.

(IV) Methyl-1-α-O-benzyl-6-O-(benzyloxycarbonyl-L-leucyl)-N-acetylmuramyl-L-valyl-D-isoglutaminate (300 mg, 0.35 mmol) was catalytically hydrogenated in acetic acid (10 ml) using palladium black as a catalyst at room temperature for 4 hours. The catalyst was removed by filtration and the solvent was removed. The residue was dissolved in methanol (0.5 ml). To this solution was added ether and the resulting powder was collected by filtration to obtain methyl 6-O-(L-leucyl)-N-acetylmuramyl-L-valyl-D-isoglutaminate (194 mg). m.p. 105°–108° C. $[\alpha]_D^{23}$ +45.3° (C 0.5, DMF). $R_f^4 = 0.28$ Elemental analysis for $C_{28}H_{49}O_{12}N_5 \cdot CH_3COOH$: Calculated: C, 50.91; H, 7.55; N, 9.90. Found: C, 50.97; H, 7.73; N, 10.00.

EXAMPLE 19

Geranylgeranylacetic acid (42 mg, 0.13 mmol) and HONB (29 mg, 0.16 mmol) were dissolved in acetonitrile (1 ml). To this solution was added DCC (33 mg, 0.16 mmol) under ice-cooling and the mixture was stirred under ice-cooling for one hour and at room temperature for 5 hours. The insoluble material was filtered and the solvent was evaporated. The resulting active ester and methyl 6-O-(L-leucyl)-N-acetylmuramyl-L-valyl-D-isoglutaminate (64.8 mg, 0.1 mmol) were dissolved in DMF (1 ml) and NEM (0.026 ml) was added. The mixture was stirred at room temperature for 15 hours and then worked-up as described in Example 2 to obtain methyl 6-O-(geranylgeranylacetyl-L-leucyl)-N-acetylmuramyl-L-valyl-D-isoglutaminate (74 mg). $[\alpha]_D^{23}$ +23.3° (C 0.5, ethanol). $R_f^2 = 0.50$ Elemental analysis for $C_{50}H_{83}O_{13}N_5 \cdot H_2O$: Calculated: C, 61.26; H, 8.74; N, 7.15. Found: C, 61.49; H, 8.70; N, 7.16.

EXAMPLE 20

Stearic acid HONB ester (223 mg, 0.5 mmol), methyl-1-α-O-benzyl-N-acetylmuramyl-L-valyl-D-isoglutaminate (156 mg, 0.25 mmol) and HOBt (13.5 mg, 1 mmol) were dissolved together with NEM (0.128 ml) in DMF (5 ml) and the mixture was stirred at room temperature for 60 hours. The reaction mixture was then worked-up as described in Example 6 (V) to obtain methyl 1-α-O-benzyl-6-O-stearoyl-N-acetylmuramyl-L-valyl-D-isoglutaminate (25 mg). m.p. 214° C. $[\alpha]_D^{24}$ +356.0° (C 0.4, chloroform), $R_f^2 = 0.79$, $R_f^3 = 0.17$.

Elemental analysis for $C_{47}H_{78}O_{12}N_4 \cdot \frac{1}{2}H_2O$: Calculated: C, 62.70; H, 8.85; N, 6.22. Found: C, 62.53; H, 8.79; N, 6.10.

EXAMPLE 21

Methyl 1-α-O-benzyl-6-O-stearoyl-N-acetylmuramyl-L-valyl-D-isoglutaminate (19.5 mg, 0.022 mmol) was dissolved in a mixture of methanol (1 ml) and acetic acid (1 ml) and catalytically hydrogenated using palladium black as a catalyst at room temperature for 5 hours. The catalyst was removed by filtration and the solvent was removed. The residue was purified by the column chromatography on Sephadex LH-20 (column size: 1.8×45 cm; elution solvent: ethanol/0.1 N acetic acid=3:2, v/v) and the fractions of the eluate 42 ml to 54 ml were collected and the solvent was removed. The residue was freeze-dried from t-butanol to obtain methyl 6-O-stearoyl-N-acetylmuramyl-L-valyl-D-isoglutaminate (13.5 mg). $[\alpha]_D^{23}$ +34.9° (C 0.5, ethanol). $R_f^2 = 0.44$, $R_f^4 = 0.58$.

Elemental analysis for $C_{40}H_{72}O_{12}N_4 \cdot 2H_2O$: Calculated: C, 57.39; H, 9.15; N, 6.69. Found: C, 57.31; H, 8.81; N, 6.89.

EXAMPLE 22

4-Phenylbutyric acid (27.1 mg, 0.165 mmol) and methyl 1-α-O-benzyl-N-acetylmuramyl-L-valyl-D-isoglutaminate (93.7 mg, 0.15 mmol) were dissolved in a mixture of DMF (0.6 ml) and pyridine (0.6 ml). DCC (46.4 mg, 0.23 mmol) was added under ice-cooling and the reaction was carried out at room temperature for 15 hours. The solvent was removed and the resulting residue was purified by the column chromatography on silica gel (column size: 1.5×12 cm; elution solvent: methanol/chloroform=5:95, v/v). The fractions containing the pure desired product were collected and the solvent was removed. The reprecipitation from methanol/ether gave methyl 1-α-O-benzyl-6-O-(4-phenylbutyroyl)-N-acetylmuramyl-L-valyl-D-isoglutaminate (83 mg). m.p. 190°–193° C. $[\alpha]_D^{21}$ +85.8° (C 0.5, DMF). $R_f^2 = 0.68$, $R_f^3 = 0.17$, $R_f^4 = 0.66$.

Elemental analysis for $C_{39}H_{54}O_{12}N_4$: Calculated: C, 60.76; H, 7.06; N, 7.27. Found: C, 60.62; H, 6.96; N, 7.21.

EXAMPLE 23

Methyl 1-α-O-benzyl-6-O-(4-phenylbutyroyl)-N-acetylmuramyl-L-valyl-D-isoglutaminate (55 mg, 0.071 mmol) was catalytically hydrogenated in acetic acid (10 ml) using palladium black as a catalyst at room temperature for 3 hours. The catalyst was filtered and the solvent was evaporated. The residue was purified by the column chromatography on Sephadex LH-20 (column size 1.5×45 cm; elution solvent: 0.1 N acetic acid/ethanol=2:3, v/v). The fractions containing the pure desired product were collected and the solvent was removed. The resulting crystals were recrystallized from ethanol/ether to obtain methyl 6-O-(4-phenyl-butyroyl)-N-acetylmuramyl-L-valyl-D-isoglutaminate (36 mg). m.p. 177° C. (dec.). $[\alpha]_D^{21}$ +42.4° (C 0.4, ethanol). $R_f^1=0.86$, $R_f^2=0.41$, $R_f^4=0.44$.

Elemental analysis for $C_{32}H_{48}O_{12}N_4.H_2O$: Calculated: C, 55.00; H, 7.21; N, 8.02. Found: C, 55.07; H, 7.13; N, 7.85.

EXAMPLE 24

5-Phenylvaleric acid (29.4 mg, 0.165 mmol) and methyl 1-α-O-benzyl-N-acetylmuramyl-L-valyl-D-isoglutaminate (93.7 mg, 0.15 mmol) were dissolved in a mixture of DMF (0.6 ml) and pyridine (0.6 ml). DCC (46.4 mg, 0.23 mmol) was added under ice-cooling. After 15 hours at room temperature, the solvent was removed. The residue was then purified in a similar manner to that described in Example 22 to obtain methyl 1-α-O-benzyl-6-O-(5-phenylvaleroyl)-N-acetylmuramyl-L-valyl-D-isoglutaminate (89 mg). m.p. 179°-180° C. $[\alpha]_D^{22}$ +82.7° (C 0.5, DMF). $R_f^2=0.67$, $R_f^3=0.18$, $R_f^4=0.63$.

Elemental analysis for $C_{40}H_{50}O_{12}N_4$: Calculated: C, 61.21; H, 7.19; N, 7.14. Found: C, 61.40; H, 7.02; N, 7.13.

EXAMPLE 25

Methyl 1-α-O-benzyl-6-O-(5-phenylvaleroyl)-N-acetylmuramyl-L-valyl-D-isoglutaminate (60 mg, 0.076 mmol) was catalytically hydrogenated in acetic acid (5 ml) using palladium black as a catalyst and then the mixture was worked-up in a similar manner to that described in Example 23 to obtain methyl 6-O-(5-phenylvaleroyl)-N-acetylmuramyl-L-valyl-D-isoglutaminate (28 mg). m.p. 176°-178° C. $[\alpha]_D^{22}$ +47.1° (C 0.4, methanol). $R_f^1=0.80$, $R_f^2=0.38$, $R_f^4=0.49$.

Elemental analysis for $C_{33}H_{50}O_{12}N_4.H_2O$: Calculated: C, 55.60; H, 7.35; N, 7.86. Found: C, 55.42; H, 7.39; N, 7.63.

EXAMPLE 26

Methyl 1-α-O-benzyl-N-acetylmuramyl-L-valyl-D-isoglutaminate (125 mg, 0.2 mmol), QS-3-OH p-nitrophenyl ester (150.1 mg, 0.4 mmol) and HOBt (108 mg, 0.8 mmol) were dissolved together with NEM (0.1 mmol) in DMF (1 ml). After 60 hours at room temperature, the reaction mixture was worked-up as described in Example 6 (V) to give methyl α-O-benzyl-6-O-(QS-3)-N-acetylmuramyl-L-valyl-D-sioglutaminate (42 mg). m.p. 189°-190° C. $[\alpha]_D^{21}$ +60.0° (C 0.5, chloroform). $R_f^2=0.70$, $R_f^3=0.20$, $R_f^5=0.11$.

Elemental analysis for $C_{41}H_{56}O_{16}N_4.\frac{1}{2}H_2O$: Calculated: C, 56.60; H, 6.61; N, 6.44. Found: C, 56.72; H, 6.66; N, 6.47.

EXAMPLE 27

Methyl-1-α-O-benzyl-6-O-(QS-3)-N-acetylmuramyl-L-valyl-D-isoglutaminate (39 mg, 0.045 mmol) was catalytically hydrogenated in methanol (5 ml) using palladium black as a catalyst at room temperature for 3 hours. The catalyst was filtered and the solvent was removed. The resulting product was oxidized with ferric chloride (500 mg) according to the procedures described in Example 7. The purification was also conducted as described in Example 7 to obtain methyl 6-O-(QS-3)-N-acetylmuramyl-L-valyl-D-isoglutaminate (39.7 mg). m.p. 167° C. $[\alpha]_D^{21}$ +42.9° (C 0.5, ethanol). $R_f^1=0.82$, $R_f^2=0.31$, $R_f^4=0.41$.

Elemental analysis for $C_{34}H_{50}O_{16}N_4.H_2O$: Calculated: C, 51.76; H, 6.65; N, 7.10. Found: C, 51.57; H, 6.63; N, 7.12.

EXAMPLE 28

(I) Ethyl 1-α-O-benzyl-N-acetylmuramyl-L-valyl-D-isoglutaminate (256 mg, 0.4 mmol), benzyloxycarbonyl-L-leucine p-nitrophenyl ester (309 mg, 0.8 mmol) and HOBt (216 mg, 16 mmol) were dissolved together with NEM (0.2 ml) in DMF (3 ml). After 60 hours at room temperature the mixture was worked-up in a similar manner to that described in Example 18 (III) to obtain ethyl 1-α-O-benzyl-6-O-(benzyloxycarbonyl-L-leucyl)-N-acetylmuramyl-L-valyl-D-isoglutaminate (261 mg). m.p. 234°-236° C. $[\alpha]_D^{23}$ +68.4° (C 0.5, DMF). $R_f^2=0.68$, $R_f^3=0.71$, $R_f^4=0.68$.

Elemental analysis for $C_{44}H_{63}O_{14}N_5$: Calculated: C, 59.64; H, 7.17; N, 7.91. Found: C, 59.54; H, 7.24; N, 7.89.

(II) Ethyl 1-α-O-benzyl-6-O-(benzyloxycarbonyl-L-leucyl)-N-acetylmuramyl-L-valyl-D-isoglutaminate (230 mg, 0.26 mmol) was catalytically hydrogenated in acetic acid (5 ml) using palladium black as a catalyst at room temperature for 5 hours. The mixture was then worked-up in a similar manner to that described in Example 18 (IV) to give ethyl 6-O-(L-leucyl)-N-acetylmuramyl-L-valyl-D-isoglutaminate (160 mg). m.p. 144°-146° C. $[\alpha]_D^{23}$ +41.2° (C 0.5, DMF). $R_f^1=0.41$, $R_f=0.55$ (n-butanol:ethyl acetate:acetic acid:water=1:1:1:1, v/v; silica gel plate, the $R_f$ value obtained under these conditions is hereinafter referred to as $R_f^6$).

Elemental analysis for $C_{29}H_{51}O_{12}N_5.CH_3COOH$: Calculated: C, 51.58; H, 7.68; N, 9.70. Found: C, 51.38; H, 7.61; N, 9.96.

EXAMPLE 29

Ethyl 6-O-(L-leucyl)-N-acetylmuramyl-L-valyl-D-isoglutaminate (53 mg, 0.08 mmol) and QS-3-OH p-nitrophenyl ester (30 mg, 0.08 mmol) were dissolved together with NEM (0.02 ml) in DMF (0.5 ml). The reaction mixture was stirred at room temperature for 60 hours and then worked-up in a similar manner to that described in Example 2 to give ethyl 6-O-(QS-3-L-leucyl)-N-acetylmuramyl-L-valyl-D-isoglutaminate (16 mg). $[\alpha]_D^{23}$ +21.1° (C 0.5, ethanol). $R_f^1=0.81$, $R_f^4=0.73$.

Elemental analysis for $C_{41}H_{63}O_{17}N_5.H_2O$: Calculated: C, 53.75; H, 7.15; N, 7.65. Found: C, 53.41; H, 7.06; N, 7.63.

EXAMPLE 30

(I) Benzyl 2-acetoamide-4,6-O-benzylidene-2-deoxy-3-O-carboxymethyl-α-D-glucopyranoside (hereinafter referred to as 1-α-O-benzyl-4,6-O-benzylidene-N- acetylnormuramic acid; 229 mg, 0.5 mmol) was dissolved together with HONB (108 mg, 0.6 mmol) in DMF (5 ml). To this solution was added DCC (124 mg, 0.6 mmol) under ice-cooling and the reaction mixture was stirred under ice-cooling for one hour and then at room temperature for 3 hours. The insoluble material was removed by filtration. Methyl L-valyl-D-isoglutaminate trifluoroacetic acid salt (obtained by treating methyl t-butyloxycarbonyl-L-valyl-D-isoglutaminate (215.6 mg. 0.6 mmol) with trifluoroacetic acid (3 ml) according to the procedures described in Example 6 (III)) together with TEA (0.1 ml) was then added. The reaction mixture was stirred at room temperature for 48 hours and evaporated. Methanol (15 ml) was added to the resulting crystalline residue, and the mixture was boiled and then cooled. The resulting crystals were collected by filtration to obtain methyl 1-α-O-benzyl-4,6-O-benzylidene-N-acetylnormuramyl-L-valyl-D-isoglutaminate (298 mg). m.p. >245° C. $[\alpha]_D^{21}$ +76.7° (C 0.4, DMF). $R_f^2$=0.68, $R_f^4$=0.60.

Elemental analysis for $C_{35}H_{46}O_{11}N_4$: Calculated: C, 60.16; H, 6.64; N, 8.02. Found: C, 60.32; H, 6.66; N, 8.03.

(II) Methyl 1-α-O-benzyl-4,6-O-benzylidene-N-acetylnormuramyl-L-valyl-D-isoglutaminate (270 mg, 0.39 mmol) was reacted in 75% acetic acid (20 ml). Then, the mixture was worked-up according to the procedures described in Example 6 (IV) to obtain methyl 1-α-O-benzyl-N-acetylnormuramyl-L-valyl-D-isoglutaminate (184 mg). m.p. 168°-170° C. $[\alpha]_D^{21}$ +73.2° (C 0.5, DMF). $R_f^2$=0.29, $R_f^4$=0.28.

Elemental analysis for $C_{28}H_{42}O_{11}N_4 \cdot H_2O$: Calculated: C, 53.49; H, 7.05; N, 8.91. Found: C, 53.39; H, 6.79; N, 8.89.

(III) Methyl 1-α-O-benzyl-N-acetylnormuramyl-L-valyl-D-isoglutaminate (61.1 mg, 0.1 mmol) and QS-10-OH (41.1 mg, 0.13 mmol) were dissolved in a mixture of DMF (0.6 ml) and pyridine (0.6 ml). To this solution was added. DCC (41.2 mg, 0.2 mmol) under ice-cooling and the reaction mixture was stirred at room temperature for 48 hours. After filtration and evaporation, the residue was purified by the column chromatography on silica gel (column size 1.5×12 cm; elution solvent:methanol/chloroform=5:95, v/v). The fractions containing the pure desired product were collected and the solvent was removed. Ether was added to the residue and the resulting crystals were filtered to obtain methyl 1-α-O-benzyl-6-O-(QS-10)-N-acetylnormuramyl-L-valyl-D-isoglutaminate (26 mg). m.p. 178° C. $R_f^2$=0.65, $R_f^3$=0.12, $R_f^4$=0.60.

Elemental analysis for $C_{47}H_{68}O_{16}N_4$: Calculated: C, 59.73; H, 7.25; N, 5.93. Found: C, 59.58; H, 7.50; N, 6.02.

EXAMPLE 31

Methyl 1-α-O-benzyl-6-O-(QS-10)-N-acetylnormuramyl-L-valyl-D-isoglutaminate (22 mg, 0.024 mmol) was catalytically hydrogenated in methanol (5 ml) using palladium black as a catalyst at room temperature for 6 hours. The catalyst was removed by filtration and the solvent was evaporated. The resulting product was oxidized with ferric chloride (250 mg) and then purified according to the procedure described in Example 7 to obtain methyl 6-O-(QS-10)-N-acetylnormuramyl-L-valyl-D-isoglutaminate (18 mg). m.p. 147° C. (dec.). $[\alpha]_D^{22}$ +20.6° (C 0.4, methanol). $R_f^1$=0.85, $R_f^2$=0.24, $R_f^3$=0.33.

Elemental analysis for $C_{40}H_{62}O_{16}N_4 \cdot H_2O$: Calculated: C, 55.03; H, 7.39; N, 6.12. Found: C, 55.21; H, 7.24; N, 6.11.

EXAMPLE 32

Benzyl 1-α-O-benzyl-N-acetylmuramyl-L-valyl-D-isoglutaminate (210 mg, 0.3 mmol) was dissolved in DMF (1.5 ml) and to the resulting solution were added QS-10-OH p-nitrophenyl ester (284 mg, 0.6 mmol), HOBt (163 mg, 1.2 mmol) and NEM (153 μl, 1.2 mmol). The mixture was stirred at room temperature for two days. After evaporation, the residue was subjected to the column chromatography on a silica gel column with a mixture of ethyl acetate/pyridine/acetic acid/water (30:10:3:5, v/v) as eluent. The fractions containing the main product were collected and the solvent was removed under reduced pressure. The residue was crystallized from a mixture of ethanol and ether to obtain benzyl 1-α-O-benzyl-6-O-(QS-10)-N-acetylmuramyl-L-valyl-D-isoglutaminate (133 mg). $[\alpha]_D^{21}$ +64.8° (C 0.5, ethanol). $R_f^3$=0.27, $R_f^4$=0.67, $R_f^5$=0.23.

Elemental analysis for $C_{54}H_{74}O_{16}N_4$: Calculated: C, 62.65; H, 7.21; N, 5.41. Found: C, 62.62; H, 7.21; N, 5.30.

EXAMPLE 33

(I) t-Butyloxycarbonyl-γ-O-benzyl-D-glutamic acid p-nitrophenyl ester (1.15 g, 2.5 mmol) was dissolved in tetrahydrofuran (5 ml). To this solution was added 0.32 ml (3 mmol) of a 30% aqueous methylamine solution under ice-cooling and the reaction mixture was stirred at room temperature for one hour. After evaporation, the residue was dissolved in ethyl acetate, washed with a 5% aqueous sodium bicarbonate solution, 1 N hydrochloric acid and saturated brine successively, and dried over anhydrous sodium sulfate. After filtration, the solvent was removed again under reduced pressure. The residue was recrystallized from a mixture of ethanol and ether to obtain t-butyloxycarbonyl-γ-O-benzyl-D-glutamic acid methylamide (1.33 g). m.p. 126°-127° C. $[\alpha]_D$ −1.4° (C 0.5, ethanol). $R_f^3$=0.61, $R_f^5$=0.71

Elementary analysis for $C_{18}H_{26}O_5N_2$: Calculated: C, 61.70; H, 7.48; N, 8.00. Found: C, 61.54; H, 7.75; N, 8.03.

(II) t-Butyloxycarbonyl-γ-O-benzyl-D-glutamic acid methylamide (1.93 g, 5.5 mmol) was catalytically hydrogenated in methanol (20 ml) in the presence of palladium black at room temperature for 3 hours. After the reaction, the catalyst was filtered off and the solvent was evaporated. The residue was recrystallized from a mixture of ethanol and petroleum ether to obtain t-butyloxycarbonyl-D-glutamic acid methylamide (1.31 g). m.p. 153° C. (dec.). $[\alpha]_D$ +3.4° (C 0.5, ethanol). $R_f^2$=0.61.

Elemental analysis for $C_{11}H_{20}O_5N_2$: Calculated: C, 50.76; H, 7.85; N, 10.76. Found: C, 50.80; H, 7.80; N, 10.69.

(III) t-Butyloxycarbonyl-D-glutamic acid methylamide (1.22 g, 4.7 mmol) was suspended in tetrahydrofuran (10 ml). To this suspension was added an ethereal solution of diazomethane until the reaction mixture turned to yellow. Excess diazomethane was decomposed by adding one drop of acetic acid and the solvent was removed under reduced pressure. The residue was recrystallized from ethyl acetate/ether/petroleum ether to obtain 1.02 g of t-butyloxycarbonyl-γ-O-methyl-D-glutamic acid methylamide (1.08 g). m.p. 94°-95° C. $[\alpha]_D^{22}$ +2.8° (C 0.5, methanol). $R_f^3$=0.43, $R_f$=0.47 (chloroform/acetone/ethanol=80:20:2, v/v; silica gel plate; the $R_f$ value obtained under these conditions is referred to as $R_f^7$).

Elemental analysis for $C_{12}H_{22}O_5N_2$: Calculated: C, 52.54; H, 8.08; N, 10.21. Found: C, 52.67; H, 8.20; N, 10.13.

(IV) t-Butyloxycarbonyl-γ-O-methyl-D-glutamic acid methylamide (1.03 g, 3.75 mmol) was dissolved in cold trifluoroacetic acid (7 ml) and the reaction was carried out at room temperature for 20 minutes. After the reaction, the solvent was removed under reduced pressure. A mixture of ether and pettroleum ether was added to the residue and the solvent was removed by the decantation. This operation was repeated twice and the residue was dried in a desiccator over sodium hydroxide under reduced pressure to obtain γ-O-methyl-D-glutamic acid methylamide trifluoroacetic acid salt.

(V) γ-O-Methyl-D-glutamic acid methylamide trifluoroacetic acid salt was dissolved in tetrahydrofuran (7 ml). To this solution was added NEM (0.48 ml) and a solution of t-butyloxycarbonyl-L-valine HONB ester (1.32 g, 3.5 mmol) in tetrahydrofuran (7 ml) under ice-cooling and the mixture was stirred at room temperature. After 16 hours, the mixture was worked-up in a manner to that described in Example 33 (I) and the residue was finally recrystallized from ethyl acetate/petroleum ether to obtain t-butyloxycarbonyl-L-valyl-γ-O-methyl-D-glutamic acid methylamide (1.17 g). m.p. 137° C. $[\alpha]_D$ +13.0° (C 0.5, ethanol). $R_f^7$=0.45.

Elemental analysis for $C_{17}H_{31}O_6N_3$: Calculated: C, 54.67; H, 8.37; N, 11.25. Found: C, 54.86; H, 8.52; N, 11.23.

(VI) t-Butyloxycarbonyl-L-valyl-γ-O-methyl-D-glutamic acid methylamide (654 mg, 175 mmol) was dissolved in cold trifluoroacetic acid (10 ml) and the mixture was stirred at room temperature. After 20 minutes, the reaction mixture was worked-up as described in Example 33 (IV) to obtain L-valyl-γ-O-methyl-D-glutamic acid methylamide trifluoroacetic acid salt. The salt thus obtained was dissolved in tetrahydrofuran (10 ml). To this solution were added a solution of 1-α-O-benzyl-4,6-O-benzylidene-N-acetylmuramic acid HONB ester (1.11 g, 1.75 mmol) in tetrahydrofuran (10 ml) and TEA (0.25 ml). The mixture was allowed to stand at room temperature overnight. The gel was filtered and the resulting solid was boiled in ethanol and then filtered again to obtain very sparingly soluble 1-α-O-benzyl-4,5-O-benzylidene-N-acetylmuramyl-L-valyl-γ-O-methyl-D-isoglutamic acid methylamide (812 mg). m.p. >280° C.

Elemental analysis for $C_{37}H_{50}O_{14}N_4$: Calculated: C, 57.35; H, 6.51; N, 7.23. Found: C, 57.49; H, 6.66; N, 7.53.

(VII) 1-α-O-Benzyl-4,6-O-benzylidene-N-acetyl-muramyl-L-valyl-γ-O-methyl-D-isoglutamic acid methylamide (727 mg, 1 mmol) was dissolved in 80% acetic acid (50 ml) and heated on a boiling water bath for 30 minutes. After the reaction, the solvent was removed under reduced pressure. The residue was recrystallized from ethanol/ether to obtain 1-α-O-benzyl-N-acetylmuramyl-L-valyl-γ-O-methyl-D-isoglutamic acid methylamide (406 mg). m.p. 237°-238° C. (dec.). $[\alpha]_D^{21}$ +118.6° (C 0.5, DMF). $R_f^4$=0.42, $R_f^6$=0.60.

Elemental analysis for $C_{36}H_{46}O_{11}N_4$: Calculated: C, 56.41; H, 7.26; N, 8.77. Found: C, 56.18; H, 7.33; N, 8.58.

(VIII) 1-α-O-Benzyl-N-acetylmuramyl-L-valyl-γ-O-methyl-D-isoglutamic acid methylamide (319 mg, 0.5 mmol), benzyloxycarbonyl-L-leucine p-nitrophenyl ester (773 mg, 2 mmol), HOBt (270 mg, 2 mmol) and NEM (668 μl) were dissolved in DMF (3.5 ml) and the mixture was stirred at room temperature. After three days, the solvent was removed under reduced pressure. The residue was dissolved in chloroform and ether was added. The resulting precipitate was filtered, washed thoroughly with ether and dried to obtain 527 mg of a white solid. The solid thus obtained was subjected to the column chromatography on silica gel with a mixture of chloroform and methanol (18:1, v/v) as eluent. The solvent was changed to a mixture of chloroform acetone and methanol (10:3:2, v/v) when the main fraction started to elute to obtain 1-α-O-benzyl-6-O-(benzyloxycarbonyl-L-leucyl)-N-acetylmuramyl-L-valyl-γ-O-methyl-D-glutamic acid methylamide (334 mg). m.p. 216°-217° C. (dec.). $[\alpha]_D$ +75.2° (C 0.5, DMF). $R_f^3$=0.15, $R_f^4$=0.78.

Elemental analysis for $C_{44}H_{63}O_{14}N_5$: Calculated: C, 59.64; H, 7.17; N, 7.90. Found: C, 59.59; H, 7.18; N, 7.88.

(IX) 1-α-O-Benzyl-6-O-(benzyloxycarbonyl-L-leucyl)-N-acetylmuramyl-L-valyl-γ-O-benzyl-D-glutamic acid methylamide (133 mg, 0.15 mmol) was catalytically hydrogenated in acetic acid (1 ml) using palladium black as a catalyst at room temperature for one hour. The catalyst was removed by filtration and the solvent was evaporated under reduced pressure. The residue was chromatographed on a Sephadex LH-20 column (1.8×44 cm) with ethanol/0.1 N acetic acid (3:2, v/v) as eluent and the fractions containing the product were collected. After evaporation, the residue was dissolved in water and freeze dried to obtain 6-O-L-leucyl-N-acetylmuramyl-L-valyl-γ-O-methyl-D-glutamic acid methylamide (96 mg). $[\alpha]_D^{21}$ +48.4° (C 0.6, DMF). $R_f^4$=0.73.

Elemental analysis for $C_{29}H_{51}O_{12}N_5 \cdot H_2O$: Calculated: C, 51.24; H, 7.86; N, 10.30. Found: C, 51.28; H, 8.04 N, 9.76.

EXAMPLE 34

6-O-L-Leucyl-N-acetylmuramyl-L-valyl-γ-O-methyl-D-glutamic acid methylamide (52.9 mg, 0.08 mmol) and QS-10-OH p-nitrophenyl ester (37.9 mg, 0.08 mmol) were dissolved in DMF (1 ml). To this solution was added NEM (21 μl, 0.16 mmol) and the resulting solution was reacted with stirring for 16 hours. After the reaction, the solvent was removed under reduced pressure. The residue was dissolved in a small amount of a mixture of chloroform and methanol (18:1, v/v) and subjected to the column chromatography on a silicagel column with a mixture of chloroform/acetone/ethanol (10:3:2, v/v) as eluent. The fractions containing the product were collected and the solvent was removed. The residue was freeze-dried from t-butanol. The resulting residue was further purified by the column chromatography on a Sephadex LH-20 column (1.8×44 cm) with a mixture of ethanol and 0.1 N acetic acid (3:2, v/v) as eluent to obtain 6-O-(QS-10-L-leucyl)-N-acetylmuramyl-L-valyl-γ-O-methyl-D-glutamic acid methylamide (50 mg). $[\alpha]_D$ +24.4° (C 0.5, ethanol). $R_f^2$=0.53.

Elemental analysis for $C_{48}H_{77}O_{17}N_5 \cdot 3/2H_2O$: Calculated: C, 56.34; H, 7.88; N, 6.85. Found: C, 56.64; H, 7.71; N, 6.76.

EXAMPLE 35

QS-10-OH p-nitrophenyl ester (379 mg, 0.8 mmol), 1-α-O-benzyl-N-acetylmuramyl-L-valyl-D-isoglutaminate (250 mg, 0.4 mmol), HOBt (216 mg, 1.6 mmol) and NEM (205 mg, 1.6 mmol) were dissolved in DMF (2 ml) and the mixture was stirred at room temperature for two days. After evaporation, the residue was purified by the column chromatography on a silica gel column with a mixture of chloroform/methanol/acetic acid (18:2:1, v/v) as eluent. The main fractions were collected and the solvent was removed. The residue was dissolved in ethanol and purified by the column chromatography on a Saphadex LH-20 column (1.5×90 cm) with ethanol as eluent. The main fractions were collected and the solvent was removed. The residue was freeze-dried from t-butanol to obtain methyl 1-α-O-benzyl-6-O-(QS-10)-N-acetylmuramyl-L-valyl-D-isoglutaminate (191 mg). $[\alpha]_D^{21}$ +70.2° (C 0.5, methanol). $R_f^2=0.64$.

Elemental analysis for $C_{48}H_{70}O_{16}N_4 \cdot \frac{1}{2}H_2O$: Calculated: C, 59.55; H, 7.39; N, 5.79. Found: C, 59.87; H, 6.99; N, 6.14.

EXAMPLE 36

Methyl 1-α-O-benzyl-6-O-(QS-10)-N-acetylmuramyl-L-valyl-D-isoglutaminate (100 mg) was catalytically hydrogenated in methanol using palladium black as a catalyst at room temperature for two hours. The catalyst was removed by filtration and the solvent was evaporated under reduced pressure. The resulting methyl 6-O- 10-(2,3-dimethoxy-5-methyl-1,4-hydroquinon-6-yl)decanoyl -N-acetylmuramyl-L-valyl-D-isoglutaminate (the dihydro form of the desired product) was dissolved in methanol (10 ml). To this was added a solution of ferric chloride (1 g) in water (2 ml) and the mixture was stirred at room temperature for 30 minutes. After the reaction, ethyl acetate (50 ml) was added and the mixture was stirred thoroughly before removing the aqueous layer. The ethyl acetate layer was washed with water (15 ml), dried over anhydrous sodium sulfate and the solvent was evaporated under reduced pressure. The resulting crystalline residue was purified by the column chromatography on a Sephadex LH-20 column (1.8×44 cm) with ethanol/0.1 N acetic acid (3:2, v/v) as eluent. The main fractions were collected and the solvent was evaporated under reduced pressure. The residue was recrystallized from a mixed solvent of ethanol/ether/petroleum ether to obtain methyl 6-O-(QS-10)-N-acetylmuramyl-L-valyl-D-isoglutaminate (52 mg). m.p. 188°–189° C. $[\alpha]_D^{21}$ +35.2° (C 0.5, ethanol). $R_f^2=0.40$, $R_f^4=0.53$.

Elemental analysis for $C_{41}H_{64}O_{16}N_4$: Calculated: C, 56.67; H, 7.42; N, 6.45. Found: C, 56.47; H, 7.42; N, 6.43.

EXAMPLE 37

6-O-(QS-3-β-Alanyl)-N-acetylmuramyl-L-alanyl-D-isoglutamine (50 mg) was dissolved in methanol (1 ml). To this solution was added a slightly excess amount of an ethereal solution of diazomethane under ice-cooling and the reaction was carried out at 0° C. for 30 minutes. After the reaction, the solvent was evaporated under reduced pressure. The residue was subjected to the column chromatography on silica gel with a mixture of ethyl acetate/pyridine/water/acetic acid (75:10:3, v/v) as eluent. The main fractions were collected and the solvent was evaporated under reduced pressure. The residue was subjected to the column chromatography on a Sephadex LH-20 column (1.8×44 cm) with a mixture of ethanol/0.1 N acetic acid (3:2, v/v) as eluent. The main fractions were collected and the solvent was evaporated under reduced pressure. The residue was freeze-dried from t-butanol to obtain methyl 6-O-(QS-3-β-alanyl)-N-acetylmuramyl-L-alanyl-D-isoglutaminate (32.7 mg). $[\alpha]_D^{21}$ +26.8° (C 0.5, ethanol). $R_f^1=0.48$, $R_f^4=0.14$, $R_f^6=0.56$.

Elemental anaysis for $C_{35}H_{51}O_{17}N_5 \cdot 3/2H_2O$: Calculated: C, 49.99; H, 6.47; N, 8.32. Found: C, 50.17; H, 6.40; N, 8.00.

EXAMPLE 38

6-O- Di(farnesylfarnesyl)acetyl-L-leucyl -N-acetylmuramyl-α-aminoisobutyryl-D-isoglutamine (15 mg, 0.01 mmol) dissolved in methanol (0.5 ml) was reacted with an ethereal solution of diazomethane in a similar manner to that described in Example 37 to obtain methyl 6-O- di(farnesylfarnesyl)acetyl-L-leucyl -N-acetylmuramyl-α-aminoisobutyryl-D-isoglutaminate (12 mg). $[\alpha]_D^{23}$ +13.8° (C 0.3, ethanol). $R_f^2=0.81$.

Elemental analysis for $C_{89}H_{145}O_{14}N_5 \cdot H_2O$: Calculated: C, 70.74; H, 9.81; N, 4.64. Found: C, 71.01; H, 9.77; N, 4.53.

EXAMPLE 39

(I) Benzyloxycarbonylglycine p-nitrophenyl ester (495 mg, 1.5 mmol), methyl 1-α-O-benzyl-N-acetylmuramyl-L-valyl-D-isoglutaminate (208 mg, 0.33 mmol), HOBt (405 mg, 3 mmol) and NEM (768 μl, 6 mmol) were reacted in DMF (2 ml) in a similar manner to that described in Example 35 to obtain methyl 1-α-O-benzyl-6-O-benzyloxycarbonylglycyl-N-acetylmuramyl-L-valyl-D-isoglutaminate (159 mg). $[\alpha]_D$ +84.8° (C 0.5, DMF). $R_f^4=0.57$.

Elemental analysis for $C_{39}H_{53}O_{14}N_5$: Calculated: C, 57.41; H, 6.55; N, 8.59. Found: C, 57.35; H, 6.58; N, 8.13.

(II) Methyl 1-α-O-benzyl-6-O-benzyloxycarbonylglycyl-N-acetylmuramyl-L-valyl-D-isoglutaminate (110 mg, 0.135 mmol) was subjected to hydrogenolysis in acetic acid using palladium black as a catalyst by the similar procedures to that described in Example 33 (IX) to obtain methyl 6-O-glycyl-N-acetylmuramyl-L-valyl-D-isoglutaminate (64.3 mg). $[\alpha]_D$ +36.8° (C 0.4, 95% ethanol). $R_f^6=0.50$.

Elemental analysis for $C_{24}H_{41}O_{12}N_5 \cdot H_2O$: Calculated: C, 47.28; H, 7.11; N, 11.49. Found: C, 47.60; H, 7.13; N, 11.55.

EXAMPLE 40

Methyl 6-O-glycyl-N-acetylmuramyl-L-valyl-D-isoglutaminate (53.3 mg, 0.09 mmol) was dissolved in DMF (0.3 ml). To this solution were added NEM (38.4 μl) and QS-10-OH p-nitrophenyl ester (47.4 mg, 0.1 mmol) successively, and the reaction mixture was allowed to stand at room temperature for two days. The work-up similar to that described in Example 3 gave methyl 6-O-(QS-10-glycyl)-N-acetylmuramyl-L-valyl-D-isoglutaminate (20 mg). $[\alpha]_D^{22}$ +23.0° (C 0.5, ethanol). $R_f^4=0.70$, $R_f^6=0.64$ Elemental analysis for $C_{43}H_{67}O_{17}N_5 \cdot H_2O$: Calculated: C, 54.71; H, 7.37; N, 7.42. Found: C, 54.69; H, 7.51; N, 7.69.

EXAMPLE 41

6-O-(QS-10-L-leucyl)-N-acetylmuramyl-L-valyl-D-isoglutamine (20 mg) dissolved in methanol (0.3 ml) was reacted with diazomethane in a similar manner to that described in Example 37 to obtain methyl 6-O-(QS-10-L-leucyl)-N-acetylmuramyl-L-valyl-D-isoglutaminate (13.8 mg). $[=]_D^{21}$ +20.5° (C 0.5, ethanol). $R_f^4=0.91$, $R_f^6=0.86$.

Elemental analysis for $C_{56}H_{75}O_{17}N_5 \cdot H_2O$: Calculated: C, 56.44; H, 7.76; N, 7.00. Found: C, 56.71; H, 7.82; N, 6.81.

EXAMPLE 42

(I) t-Butyloxycarbonyl-γ-O-methyl-D-glutamic acid N-hydroxysuccinimide ester (1.08 g, 3 mmol) was dissolved in acetonitrile (5 ml). To this solution was added a 30% aqueous ethylamine solution with cooling. The workup similar to that described in Example 33 (I) gave t-butyloxycarbonyl-γ-O-methyl-D-glutamic acid ethylamide (0.75 g). m.p. 77° C. $[\alpha]_D^{22}$ +6.0° (C 0.5, ethanol). $R_f^5 = 0.70$.

Elemental analysis for $C_{12}H_{24}O_5N_2$: Calculated: C, 54.15; H, 8.39; N, 9.72. Found: C, 54.50; H, 8.45; N, 9.74.

(II) After being treated with trifluoroacetic acid, t-butyloxycarbonyl-γ-O-methyl-D-glutamic acid ethylamide (692 mg, 2.4 mmol) was reacted with t-butyloxycarbonyl-L-valine HONB ester (757 mg, 2 mmol) in a similar manner to that described in Example 33 (V) to obtain t-butyloxycarbonyl-L-valyl-γ-O-methyl-D-glutamic acid ethylamide (623 mg). m.p. 154°–156° C. $[\alpha]_D^{22}$ +15.8° C. (C 0.5, ethanol). $R_f^3 = 0.53$.

Elemental analysis for $C_{18}H_{33}O_6N_3$: Calcuated: C, 55.79; H, 8.59; N, 10.85. Found: C, 55.66; H, 8.97; N, 10.88.

(III) After being treated with cold trifluoroacetic acid (5 ml), t-butyloxycarbonyl-L-valyl-γ-O-methyl-D-glutamic acid ethylamide (581 mg, 1.5 mmol) was reacted with 1-α-O-benzyl-4,6-O-benzylidene-N-acetylmuramic acid HONB ester (984 mg, 1.5 mmol) in tetrahydrofuran in the presence of TEA (0.21 ml, 1.5 mmol) in a similar manner to that described in Example 33 (VI) to obtain very sparingly soluble 1-γ-O-benzyl-4,6-O-benzylidene-N-acetylmuramyl-L-valyl-γ-O-methyl-D-glutamic acid ethylamide (1.03 g) m.p. >280° C.

Elemental analysis for $C_{38}H_{52}O_{11}N_4$: Calculated: C, 61.60; H, 7.08; N, 7.56. Found: C, 61.38; H, 6.98; N, 7.55.

(IV) 1-α-O-Benzyl-4,6-O-benzylidene-N-acetylmuramyl-L-valyl-γ-O-methyl-D-glutamic acid ethylamide (741 mg, 1 mmol) in a mixture of acetic acid (30 ml) and water (5 ml) was treated as described in Example 33 (VII). The final product, 1-α-O-benzyl-N-acetylmuramyl-L-valyl-γ-O-methyl-D-glutamic acid ethylamide, was separated as a gel from 90% ethanol/ethyl acetate/ether: 503 mg. $[\alpha]_D$ +115.4° (C 0.5, DMF). $R_f^4 = 0.73$.

Elemental analysis for $C_{24}H_{42}O_{11}N_4 \cdot \frac{1}{2}H_2O$ Calculated: C, 56.26; H, 7.46; N, 8.47. Found: C, 56.51; H, 7.41; N, 8.46.

(V) A mixture of 1-α-O-benzyl-N-acetylmuramyl-L-valyl-γ-O-methyl-D-glutamic acid ethylamide (84 mg, 0.15 mmol), QS-10-OH p-nitrophenyl ester (142 mg, 0.3 mmol), HOBt (81 mg, 0.6 mmol) and NEM (77 μl, 0.6 mmol) in DMF (2 ml) was stirred and then worked-up in a similar manner to that described in Example 33 (VIII) to obtain 1-α-O-benzyl-6-O-(QS-10)-N-acetylmuramyl-L-valyl-γ-O-methyl-D-glutamic acid ethylamide (76.2 mg). m.p. 213°–214° C. (dec.). $[\alpha]_D$ +75.8° (C 0.5, ethanol). $R_f^3 = 0.26$, $R_f^4 = 0.80$.

Elemental analysis for $C_{50}H_{74}O_{16}N_4 \cdot \frac{1}{2}H_2O$: Calculated: C, 60.28; H, 7.59; N, 5.63. Found: C, 60.17; H, 7.53; N, 5.76.

EXAMPLE 43

1-α-O-Benzyl-6-O-(QS-10)-N-acetylmuramyl-L-valyl-γ-O-methyl-D-glutamic acid ethylamide (50 mg) was catalytically hydrogenated in methanol (3 ml) using palladium black as a catalyst at room temperature for 8 hours and then oxidized with a solution of ferric chloride (0.5 g) in water (1 ml) as described in Example 36 to obtain 6-O-(QS-10)-N-acetylmuramyl-L-valyl-γ-O-methyl-D-glutamic acid ethylamide (26.2 mg). m.p. 194°–195° C. (dec.). $[\alpha]_D$ +37.0° (C 0.5, ethanol). $R_f^3 = 0.11$, $R_f^4 = 0.75$.

Elemental analysis for $C_{43}H_{68}O_{16}N_4$: Calculated: C, 57.57; H, 7.64; N, 6.25. Found: C, 57.49; H, 7.67; N, 6.29.

EXAMPLE 44

(I) t-Butyloxycarbonyl-O-benzyl-L-serine (738 mg, 2.5 mmol) and HONB (448 mg, 2.5 mmol) were dissolved in acetonitrile (10 ml). To this solution was added DCC (516 mg, 2.5 mmol) under cooling, and the mixture was stirred at 0° C. for 2 hours and then at room temperature for 14 hours. The insoluble material was removed by filtration and the solvent was evaporated under reduced pressure to obtain t-butyloxycarbonyl-O-benzyl-L-serine HONB active ester as a syrup.

Methyl t-butyloxycarbonyl-D-isoglutaminate (651 mg, 2.5 mmol) was treated with cold trifluoroacetic acid (5 ml) in a similar manner to that described in Example 33 (IV) to obtain methyl D-isoglutaminate trifluoroacetic acid salt. This salt was then dissolved in ethyl acetate (5 ml), and neutralized by adding TEA (0.35 ml) with cooling. To the resulting solution was added a solution of t-butyloxycarbonyl-O-benzyl-L-serine HONB active ester in ethyl acetate (5 ml), and the reaction was carried out at room temperature for 16 hours. The work-up similar to that described in Example 33 (I) and recrystallization from ethyl acetate/ether gave methyl t-butyloxycarbonyl-O-benzyl-L-seryl-D-isoglutaminate (0.78 g). m.p. 103°–104° C. $[\alpha]_D^{22}$ +7.0 (C 0.5, ethanol). $R_f^5 = 0.40$.

Elemental analysis for $C_{21}H_{31}O_7N_3$: Calculated: C, 57.65; H, 7 14; N, 9.61. Found: C, 57.70; H, 7.15; N, 9.55.

(II) Methyl t-butyloxycarbonyl-O-benzyl-L-seryl-D-isoglutaminate (438 mg, 1 mmol) was treated with cold trifluoroacetic acid (6 ml) in a similar manner to that described in Example 33 (IV) and dissolved in tetrahydrofuran (4 ml). The solution was then neutralized with TEA (0.14 ml) under ice-cooling. To the resulting solution was added a solution of 1-α-O-benzyl-4,6-O-benzylidene-N-acetylmuramic acid HONB ester (633 mg, 1 mmol) in tetrahydrofuran (2 ml) and the mixture was stirred at room temperature for 16 hours. Further, TEA (0.14 ml) was added and the mixture was stirred at room temperature for 4 hours. The formed gel was filtered, washed with tetrahydrofuran thoroughly and dried. The solid thus obtained was heated in DMF (2 ml) on a boiling water bath. After the addition of ethanol (4 ml), the mixture was allowed to stand overnight in a refrigerator. The formed gel was filtered to obtain methyl 1-α-O-benzyl-4,6-O-benzylidene-N-acetylmuramyl-O-benzyl-L-seryl-D-isoglutaminate (548 mg). m.p. 277°–278° C. $[\alpha]_D^{21}$ +92.0° (C 0.5, DMF). $R_f^2 = 0.79$, $R_f^4 = 0.70$.

Elemental analysis for $C_{41}H_{50}O_{12}N_4$: Calculated: C, 62.26; H, 6.37; N, 7.09. Found: C, 62.25; H, 6.35; N, 7.15.

(III) Methyl 1-α-O-benzylidene-N-acetylmuramyl-O-benzyl-L-seryl-D-isoglutaminate (395 mg, 0.5 mmol) was heated in 60% acetic acid (40 ml) for 15 minutes. The mixture was then worked-up in a similar manner as to that described in Example 33 (VII) to obtain methyl 1-α-O-benzyl-N-acetylmuramyl-O-benzyl-L-seryl-D-isoglutaminate (291 mg). m.p. 224°–225° C. $[\alpha]_D^{21}$ +99.2° (C 0.5, DMF). $R_f^2 = 0.27$, $R_f^4 = 0.32$.

Elemental analysis for $C_{34}H_{46}O_{12}N_4$: Calculated: C, 58.10; H, 6.60; N, 7.97. Found: C, 57.96; H, 6.51; N, 8.22.

(IV) Methyl 1-α-O-benzyl-N-acetylmuramyl-O-benzyl-L-seryl-D-isoglutaminate (93.4 mg, 0.15 mmol), QS-10-OH p-nitrophenyl ester (142.1 mg, 0.3 mmol), HOBt (81.1 mg, 0.6 mmol) and NEM (76.8 µl, 0.6 mmol) were dissolved in DMF (1 ml). The mixture was stirred at room temperature for 40 hours. After evaporation, the residue was subjected to the silica gel column chromatography with chloroform as eluent. When the orangy-yellow substance was eluted out, the eluent was changed to a mixture of chloroform/methanol (19:1, v/v), and the main fractions were collected. After evaporation, the residue was crystallized from ethanol/ether to obtain methyl 1-α-O-benzyl-6-O-(QS-10)-N-acetylmuramyl-O-benzyl-L-seryl-D-isoglutaminate (99.3 mg). m.p. 163°–165° C. (dec.). $[\alpha]_D^{21}$ +65.4° (C 0.5, ethanol). $R_f^2=0.63$, $R_f^3=0.23$, $R_f^4=0.65$.

Elemental analysis for $C_{53}H_{72}O_{17}N_4$: Calculated: C, 61.37; H, 7.00; N, 5.40. Found: C, 61.67; H, 7.15; N, 5.13.

EXAMPLE 45

According to the procedure described in Example 36, methyl 1-α-O-benzyl-6-O-(QS-10)-N-acetylmuramyl-O-benzyl-L-seryl-D-isoglutaminate (72.6 mg, 0.07 mmol) was catalytically hydrogenated in methanol (1 ml) in the presence of palladium black and then oxidized with ferric chloride (750 mg) to obtain methyl 6-O-(QS-10)-N-acetylmuramyl-L-seryl-D-isoglutaminate (35.9 mg). m.p. 149°–150° C. $[\alpha]_D^{22}$ +39.2° (C 0.5, methanol). $R_f^1=0.79$, $R_f^2=0.19$, $R_f^4=0.22$.

Elemental analysis for $C_{39}H_{60}O_{17}N_4$: Calculated: C, 54.66; H, 7.06; N, 6.54. Found: C, 54.81; H, 7.01; N, 6.80.

EXAMPLE 46

(I) Methyl t-butyloxycarbonyl-D-isoglutaminate (0.65 g, 2.5 mmol) and t-butyloxycarbonyl-O-benzyl-L-threonine (0.77 g, 2.5 mmol) were reacted by the similar procedure to that described in Example 44 (I) to obtain methyl t-butyloxycarbonyl-O-benzyl-L-threonyl-D-isoglutaminate (0.73 g). m.p. 131°–132° C. $[\alpha]_D^{22}$ +7.0° (C 0.5, ethanol). $R_f^3=0.39$, $R_f^5=0.46$.

Elemental analysis for $C_{22}H_{33}O_7N_3$: Calculated: C, 58.52; H, 7.37; N, 9.31. Found: C, 58.71; H, 7.43; N, 9.25.

(II) Methyl t-butyloxycarbonyl-O-benzyl-L-threonyl-D-isoglutaminate (0.45 g, 1 mmol) and 1-α-O-benzyl-4,6-O-benzylidene-N-acetylmuramic acid HONB ester (0.63 g, 1 mmol) were treated by the similar procedure to that described in Example 44 (II) to obtain methyl 1-α-O-benzyl-4,6-O-benzylidene-N-acetylmuramyl-O-benzyl-L-threonyl-D-isoglutaminate (356 mg). m.p. 221° (dec.). $[\alpha]_D^{21}$ +92.0° (C 0.5, DMF). $R_f^4=0.73$.

Elemental analysis for $C_{42}H_{52}O_{12}N_4$: Calculated: C, 62.67; H, 6.51; N, 6.96. Found: C, 62.27; H, 6.44; N, 7.20.

(III) Methyl 1-α-O-benzyl-4,6-O-benzylidene-N-acetylmuramyl-O-benzyl-L-threonyl-D-isoglutaminate (281.7 mg) was treated in 60% acetic acid (30 ml) in a similar manner to that described in Example 44 (III) to obtain methyl 1-α-O-benzyl-N-acetylmuramyl-O-benzyl-L-threonyl-D-isoglutaminate (215.1 mg). m.p. 181°–182° C. $[\alpha]_D^{21}$ +102.4° (C 0.5, DMF). $R_f^2=0.34$, $R_f^4=0.45$.

Elemental analysis for $C_{35}H_{48}O_{12}N_4\cdot\frac{1}{2}H_2O$: Calculated: C, 57.91; H, 6.81; N, 7.72. Found: C, 57.95; H, 6.66; N, 7.65.

(IV) Methyl 1-α-O-benzyl-N-acetylmuramyl-O-benzyl-L-threonyl-D-isoglutaminate (95.5 mg, 0.15 mmol) and QS-10-OH p-nitrophenyl ester (142.1 mg, 0.3 mmol) were reacted in DMF (1 ml) in the presence of HOBt (81.1 mg, 0.6 mmol) and NEM (76.8 µl, 0.6 mmol) according to the procedure described in Example 44 (IV) to obtain methyl 1-α-O-(QS-10)-N-acetylmuramyl-O-benzyl-L-threonyl-D-isoglutaminate (89.3 mg). m.p. 143° C. $[\alpha]_D^{21}$ +59.6° (C 0.5, ethanol), $R_f^2=0.76$, $R_f^3=0.17$, $R_f^4=0.67$ Elemental analysis for $C_{54}H_{74}O_{17}N_4\cdot\frac{1}{2}H_2O$: Calculated: C, 61.17; H, 7.13; N, 5.29. Found: C, 61.02; H, 7.05; N, 5.40.

EXAMPLE 47

Methyl 1-α-O-benzyl-6-O-(QS-10)-N-acetylmuramyl-O-benzyl-L-threonyl-D-isoglutaminate (73.6 mg, 0.07 mmol) was catalytically hydrogenated in methanol (1 ml) in the presence of palladium black and then oxidized with ferric chloride (750 mg) according to the same procedure described in Example 45 to obtain methyl 6-O-(QS-10)-N-acetylmuramyl-L-threonyl-D-isoglutaminate (421 mg). m.p. 147°–148° C. $[\alpha]_D^{21}$ +37.2° (C 0.5, methanol).

Elemental analysis for $C_{40}H_{62}O_{17}N_4$: Calculated: C, 55.16; H, 7.18; N, 6.43. Found: C, 55.38; H, 7.40; N, 6.79.

EXAMPLE 48

10-(2-Hydroxy-3,4-dimethoxy-6-methylphenyl)-decanoic acid (236.9 mg, 0.7 mmol) and p-nitrophenol (107.1 mg, 0.77 mmol) were dissolved in acetonitrile (2 ml). To this solution was added DCC (158.9 mg, 0.77 mmol) under ice-cooling. The solution was stirred at room temperature for 16 hours. The insoluble material was removed by filtration and the solvent was evaporated under reduced pressure. The residue was chromatographed on a silica gel column with chloroform as eluent to obtain about 5 m mol of 10-(2-hydroxy-3,4-dimethoxy-6-methylphenyl)decanoic acid p-nitrophenyl ester. The ester was dissolved in DMF (1.5 ml). To this solution was added methyl 1-α-O-benzyl-N-acetylmuramyl-L-valyl-D-isoglutaminate (0.15 g, 0.25 mmol), HoBt(0.14 g, 1 mmol) and NEM (128 µl, 1 mmol) and the reaction mixture was stirred at room temperature for four days. After evaporation, the residue was purified by the chromatography on a silica gel column with chloroform/acetone/methanol (10:3:1, v/v) as eluent and precipitated as a gel from ethanol/ether to obtain methyl 1-α-O-benzyl-6-O-{10-(2-hydroxy-3,4-dimethoxy-6-methylphenyl)decanoyl}-N-acetylmuramyl-L-valyl-D-isoglutaminate (0.13 g). $[\alpha]_D^{22}$ +71.8° (C 0.5, DMF). $R_f^4=0.70$.

Elemental analysis for $C_{48}H_{72}O_{15}N_4$: Calculated: C, 61.00; H, 7.68; N, 5.93. Found: C, 60.62; H, 7.62; N, 5.81.

EXAMPLE 49

Methyl 1-α-O-benzyl-6-O-{10-(2-hydroxy-3,4-dimethoxy-6-methylphenyl)decanoyl}-N-acetylmuramyl-L-valyl-D-isoglutaminate (70 mg, 0.074 mmol) was catalytically hydrogenated in methanol (1 ml) using palladium black as a catalyst at room temperature for 14 hours. After filtration and evaporation, the residue was reprecipitated from ethanol/ether to obtain methyl 6-O-{10-(2-hydroxy-3,4-dimethoxy-6-methylphenyl)-decanoyl}-N-acetylmuramyl-L-valyl-D-isoglutaminate (39.2 mg). $[\alpha]_D^{21}$ +40.8° (C 0.5, ethanol). $R_f^4=0.41$ Elemental analysis for $C_{41}H_{66}O_{15}N_4$: Calculated: C, 57.59; H, 7.78; N, 6.55. Found: C, 57.24; H, 7.87; N, 6.51.

EXAMPLE 50

(I) Benzyloxycarbonyl-ε-aminocaproic acid p-nitrophenyl ester (271 mg, 0.7 mmol), methyl 1-α-O- benzyl-N-acetylmuramyl-L-valyl-D-isoglutaminate (219 mg, 0.35 mmol), HOBt (189 mg, 1.4 mmol) and NEM (179 μl, 1.4 mmol) were dissolved in DMF (2 ml). After being stirred at room temperature for three days, the mixture was condensed to obtain a syrup. The residue which was solidified by adding ether was then chromatographed on a silica gel column with chloroform/acetone/methanol (10:3:1, v/v) as eluent. The main fractions were collected and the solvent was removed. The residue was precipitated as a gel from ethanol/ether to obtain methyl 1-α-O-benzyl-6-O-(benzyloxycarbonyl-ε-aminocaproyl)-N-acetylmuramyl-L-valyl-D-isoglutaminate (219 mg). $[\alpha]_D^{21}$ +78.6° (C 0.5, DMF). $R_f^4 = 0.56$.

Elemental anslysis for $C_{43}H_{61}O_{14}N_5$: Calculated: C, 59.23; H, 7.05; N, 8.03. Found: C, 59.26; H, 7.10; N, 8.25.

(II) Methyl 1-α-O-benzyl-6-O-(benzyloxycarbonyl-aminocaproyl)-N-acetylmuramyl-L-valyl-D-isoglutaminate (174 mg, 0.2 mmol) was catalytically hydrogenated in methanol (2 ml) using palladium black as a catalyst at room temperature for 5 hours. The purification in a similar manner to that described in Example 49 gave methyl 6-O-(ε-aminocaproyl)-N-acetylmuramyl-L-valyl-D-isoglutaminate (97 mg). $[\alpha]_D^{21}$ +39.6° (C 0.5, ethanol). $R_f^1 = 0.09$.

Elemental analysis for $C_{28}H_{49}O_{12}N_5 \cdot \frac{1}{2}H_2O$:
Calculated: C, 51.21; H, 7.68; N, 10.67. Found: C, 51.46; H, 7.84; N, 10.61.

EXAMPLE 51

(I) According to the procedure described in Example 50 (I), benzyloxycarbonyl-11-aminoundecanoic acid p-nitrophenyl ester (326 mg, 0.7 mmol) and methyl 1-α-O-benzyl-N-acetylmuramyl-L-valyl-D-isoglutaminate (219 mg, 0.35 mmol) were reacted in DMF (2 ml) in the presence of HOBt (189 mg, 1.4 mmol) and NEM (179 μl, 1.4 mmol) to obtain methyl 1-α-O-benzyl-6-O-(benzyloxycarbonyl-11-amino-undecanoyl)-N-acetylmuramyl-L-valyl-D-isoglutaminate (225 mg). $[\alpha]_D^{22}$ +74.4° (C 0.5, DMF). $R_f^4 = 0.65$.

Elemental analysis for $C_{48}H_{71}O_{14}N_5$: Calculated: C, 61.19; H, 7.60; N, 7.44. Found: C, 61.22; H, 7.72; N, 7.60.

(II) According to the procedure described in Example 50 (II), methyl 1-α-O-benzyl-6-O-(benzyloxycarbonyl-11-aminoundecanoyl)-N-acetylmuramyl-L-valyl-D-isoglutaminate (141 mg, 0.15 mmol) was catalytically hydrogenated in methanol (1 ml) using palladium black as a catalyst to obtain methyl 6-O-(11-aminoundecanoyl)-N-acetylmuramyl-L-valyl-D-isoglutaminate (89 mg). $[\alpha]_D^{21}$ +41.5° (C 0.5, ethanol).

Elemental analysis for $C_{33}H_{59}O_{12}N_5 \cdot H_2O$: Calculated: C, 53.86; H, 8.36; N, 9.52. Found: C, 53.78; H, 8.13; N, 9.76.

EXAMPLE 52

Methyl 6-O-(11-aminoundecanoyl)-N-acetylmuramyl-L-valyl-D-isoglutaminate (64.6 mg, 0.09 mmol) and QS-10-OH p-nitrophenyl ester (42.6 mg, 0.09 mmol) were reacted in DMF (2 ml) in the presence of NEM (23 μl) for 16 hours to obtain a gel, to which petroleum ether was added. After filtration the resulting solid was chromatographed on a silica gel column with chloroform/acetone/methanol (10:3:1, v/v) as eluent. The main fractions were collected and the solvent was removed under reduced pressure. The residue was crystallized from ethanol/ether to obtain methyl 6-O-[(QS-10)-11-aminoundecanoyl]N-acetylmuramyl-L-valyl-D-isoglutaminate (54.1 mg). m.p. 185°–186° C. (dec.). $[\alpha]_D^{21}$ +32.6° (C 0.5, ethanol). $R_f^1 = 0.83$, $R_f^4 = 0.53$.

Elemental analysis for $C_{52}H_{85}O_{17}N_5$: Calculated: C, 59.35; H, 8.14; N, 6.66. Found: C, 59.06; H, 8.25; N, 6.44.

EXAMPLE 53

According to the procedure described in Example 52, methyl 6-O-(ε-aminocaproyl)-N-acetylmuramyl-L-valyl-D-isoglutaminate (42.1 mg, 0.065 mmol) and QS-10-OH p-nitrophenyl ester (30.8 mg, 0.065 mmol) were reacted in DMF (0.5 ml) in the presence of NEM (8.3 μl) to obtain methyl 6-O-(QS-10-ε-aminocaproyl)-N-acetylmuramyl-L-valyl-D-isoglutaminate (31.1 mg). m.p. 176°–177° C. (dec.). $[\alpha]_D^{21}$ +31.2° (C 0.5, ethanol). $R_f^1 = 0.84$, $R_f^4 = 0.47$.

Elemental analysis for $C_{47}H_{75}O_{17}N_5 \cdot \frac{1}{2}H_2O$:
Calculated: C, 56.95; H, 7.73; N, 7.07. Found: C, 56.98; H, 7.72; N, 6.91.

EXAMPLE 54

According to the procedure described in Example 52, methyl 6-O-(ε-aminocaproyl)-N-acetylmuramyl-L-valyl-D-isoglutaminate (42.1 mg, 0.065 mmol) and QS-3-OH p-nitrophenyl ester (24.4 mg, 0.065 mmol) were reacted in DMF (0.5 ml) in the presence of NEM (8.3 μl). After purification, the resulting residue was finally freeze-dried from t-butanol to obtain methyl 6-O-(QS-3-aminocaproyl)-N-acetylmuramyl-L-valyl-D-isoglutaminate (20.5 mg). $[\alpha]_D^{21}$ +32.8° (C 0.5, ethanol). $R_f^1 = 0.81$, $R_f^6 = 0.61$.

Elemental analysis for $C_{50}H_{61}O_{17}N_5$: Calculated: C, 59.81; H, 6.12; N, 6.98. Found: C, 59.75; H, 6.41; N, 7.31.

EXAMPLE 55

(I) t-Butyloxycarbonyl-γ-O-benzyl-D-glutamic acid N-hydroxysuccinimide ester (3.26 g, 7.5 mmol) was dissolved in acetonitrile (15 ml) and a solution of n-hexylamine (0.81 g, 8 mmol) in acetonitrile (5 ml) was added. The reaction was then carried out at room temperature for 16 hours. After evaporation, the residue was dissolved in ethyl acetate, washed with a 5% aqueous sodium bicarbonate solution and saturated brine successively, dried over anhydrous sodium sulfate, filtered, and evaporated. The residue was recrystallized from ethyl acetate/petroleum ether to obtain t-butyloxycarbonyl-γ-O-benzyl-D-glutamic acid n-hexylamide (2.90 g). $R_f^2 = 0.87$, $R_f^3 = 0.92$.

(II) t-Butyloxycarbonyl-γ-O-benzyl-D-glutamic acid n-hexylamide (2.63 g, 6 mmol) and t-butyloxycarbonyl-L-valine HONB ester (2.27 g, 6 mmol) were treated in a similar manner to that described in Example 33 (IV) to obtain t-butyloxycarbonyl-L-valyl-γ-O-benzyl-D-glutamic acid n-hexylamide (1.47 g). m.p. 94° C. $[\alpha]_D^{22}$ +6.8° (C 0.5, ethanol). $R_f^2 = 0.84$, $R_f^3 = 0.89$.

Elemental analysis for $C_{28}H_{45}O_6N_3$: Calculated: C, 64.71; H, 8.73; N, 8.09. Found: C, 64.51; H, 8.78; N, 8.06.

(III) t-Butyloxycarbonyl-L-vallyl-γ-O-benzyl-D-glutamic acid n-hexylamide (1.04 g, 2 mmol) was catalytically hydrogenated in methanol (20 ml) using palladium black as a catalyst at room temperature for 3 hours. The catalyst was filtered and the solvent was removed to obtain t-butyloxycarbonyl-L-valyl-D-glutamic acid α-n-hexylamide (870 mg) as a glass-like solid residue. m.p. 63°–65° C. $[\alpha]_D^{26}$ +9.84° (C 0.5, DMF). $R_f^2 = 0.68$.

Elemental analysis for $C_{21}H_{39}O_6N_3$: Calculated: C, 58,71; H, 9.15; N, 9.78. Found: C, 58.61; H, 9.23; N, 9.65.

(IV) t-Butyloxycarbonyl-L-valyl-D-glutamic acid α-n-hexylamide (840 mg, 1.96 mmol) was dissolved in ethyl acetate (15 ml) and a slightly excess ethereal solution of diazomethane was added under ice-cooling. After 30 minutes under ice-cooling, few drops of acetic acid were added. The reaction mixture was washed with a 5% aqueous sodium bicarbonate solution, 1 N hydrochloric acid and water successively, dried over anhydrous sodium sulfate, and evaporated. The crystalline residue was recrystallized from ethyl acetate/petroleum ether to obtain t-butyloxycarbonyl-L-valyl-γ-O-methyl-D-glutamic acid n-hexylamide (905 mg). m.p. 117° C. $[\alpha]_D^{26}$ +17.6° (C 0.5, DMF). $R_f^2=0.85$, $R_f^3=0.55$.

Elemental analysis for $C_{22}H_{41}O_6N_3$: Calculated: C, 59.97; H, 9.32; N, 9.47. Found: C, 59.77; H, 9.49; N, 9.39.

(V) t-Butyloxycarbonyl-L-valyl-γ-O-methyl-D-glutamic acid n-hexylamide (870 mg, 1.96 mmol) was dissolved in trifluoroacetic acid (5 ml) and the reaction was carried out at room temperature for 20 minutes. After evaporation, the oily residue was dried in a desiccator over sodium hydroxide pellets. This was then dissolved in acetonitrile (20 ml) and neutralized with TEA (0.28 ml) under cooling. Immediately after the addition of 1-α-O-benzyl-4,6-O-benzylidene-N-acetylmuramic acid HONB ester (1.23 g, 1.96 mmol), the product started to separate. The reaction was continued at room temperature for 15 hours. Thereafter, ether (70 ml) was added and the resulting crystals were filtered to obtain 1-α-O-benzyl-4,6-O-benzylidene-N-acetylmuramyl-L-valyl-γ-O-methyl-D-glutamic acid n-hexylamide (1.15 g). m.p.>260° C. $[\alpha]_D^{26}$ +69.9° (C 0.5, DMF).

Elemental analysis for $C_{42}H_{60}O_{11}N_4$: Calculated: C, 63.30; H, 7.59; N, 7.03. Found: C, 63.11; H, 7.60; N, 6.95.

(VI) 1-α-Benzyl-4,6-O-benzylidene-N-acetylmuramyl-L-valyl-γ-O-methyl-D-glutamic acid n-hexylamide (1.10 g, 1.38 mmol) was dissolved in 75% acetic acid (40 ml), heated at 100° C. for 45 minutes and the solvent was removed. The residue was flushed with water and then with toluene twice, and then recrystallized from ethanol/ether to obtain 1-α-O-benzyl-N-acetylmuramyl-L-valyl-γ-O-methyl-D-glutamic acid n-hexylamide (780 mg). m.p. 239° C. (dec.). $[\alpha]_D^{26}$ +106.3° (C 0.5, DMF). $R_f^2=0.57$, $R_f^4=0.56$.

Elemental analysis for $C_{35}H_{56}O_{11}N_4$: Calculated: C, 59.30; H, 7.96; C, 7.90. Found: C, 59.13; H, 7.95; C, 7.83.

(VII) Benzyloxycarbonylglycine p-nitrophenyl ester (396.3 mg, 1.2 mmol), 1-α-O-benzyl-N-acetylmuramyl-L-valyl-γ-O-methyl-D-glutamic acid n-hexylamide (425 mg, 0.6 mmol), 1-hydroxybenzotriazole (324 mg, 2.4 mmol) and NEM (0.31 ml, 2.4 mmol) were dissolved in DMF (7 ml). The mixture was stirred at room temperature for three days and evaporated. The residue was dissolved in chloroform and chromatographed on a silica gel column (3×13 cm) with methanol/chloroform (2.5:97.5) as eluent. The fractions of the eluate ranging from about 150 ml to about 225 ml were collected and the combined eluate was washed with a 5% aqueous sodium bicarbonate solution and water successively, dried over anhydrous sodium sulfate, and evaporated. After addition of ether and cooling, the formed crystals were collected by filtration to obtain 1-α-O-benzyl-6-O-(benzyloxycarbonylglycyl)-N-acetylmuramyl-L-valyl-γ-O-methyl-D-glutamic acid n-hexylamide (404 mg). m.p. 208° C. $[\alpha]_D^{26}$ +80.4° (C 0.5, DMF). $R_f^2=0.80$, $R_f^3=0.30$.

Elemental analysis for $C_{45}H_{65}O_{14}N_5$: Calculated: C, 60.05; H, 7.28; N, 7.78. Found: C, 59.83; H, 7.44; N, 7.65.

(VIII) 1-α-O-Benzyl-6-O-(benzyloxycarbonylglycyl)-N-acetylmuramyl-L-valyl-γ-O-methyl-D-glutamic acid n-hexylamide (200 mg, 0.22 mmol) was catalytically hydrogenated in acetic acid (10 ml) using palladium black as a catalyst at room temperature for 6 hours. The catalyst was filtered and the acetic acid was removed. The residue was freeze-dried from t-butanol to obtain 6-O-glycyl-N-acetylmuramyl-L-valyl-γ-O-methyl-D-glutamic acid n-hexylamide (140 mg). $[\alpha]_D^{26}$ +48.7° (C 0.5, DMF). $R_f^1=0.28$.

Elemental analysis for $C_{30}H_{53}O_{12}N_5 \cdot CH_3COOH$: Calculated: C, 52.08; H, 7.79; N, 9.49. Found: C, 51.84; H, 8.10; N, 9.65.

EXAMPLE 56

6-O-Glycyl-N-acetylmuramyl-L-valyl-γ-O-methyl-D-glutamic acid n-hexylamide (54.1 mg, 0.08 mmol), QS-10-OH p-nitrophenyl ester (37.9 mg, 0.08 mmol) and NEM (0.015 ml) were dissolved in DMF (0.5 ml) and the mixture was stirred at room temperature for three days. After evaporation, the residue was purified similarly as in Example 2 by the chromatography on a silica gel column and then on a Sephadex LH-20 column. The resulting residue was freeze-dried from t-butanol to obtain 6-O-(QS-10-glycyl)-N-acetylmuramyl-L-valyl-γ-O-methyl-D-glutamic acid n-hexylamide as powder (35 mg). $[\alpha]_D^{27}$ +31.8° (C 0.5, ethanol). $R_f^1=0.87$, $R_f^2=0.63$.

Elemental analysis for $C_{49}H_{79}O_{17}N_5 \cdot H_2O$: Calculated: C, 57.24; H, 7.94; N, 6.81. Found: C, 57.24; H, 7.75; N, 6.88.

EXAMPLE 57

6-O-[6-(2,3,5-trimethyl-1,4-benzoquinon-6-yl)-hexanoyl-L-leucyl]-N-acetylmuramyl-α-aminoisobutyryl-D-isoglutamine (43 mg, 0.05 mmol) was dissolved in methanol (0.5 ml), and treated with an excess ethereal solution of diazomethane in a similar manner to that described in Example 37 to obtain methyl 6-O-(6-(2,3,5-trimethyl-1,4-benzoquinon-6-yl)-hexanoyl-L-leucyl)-N-acetylmuramyl-α-aminoisobutyryl-D-isoglutaminate (31.1 mg). $[\alpha]_D^{21}$ +27.1° (C 0.5, ethanol). $R_f^1=0.53$.

Elemental analysis for $C_{42}H_{65}O_{15}N_5 \cdot H_2O$: Calculated: C, 56.17; H, 7.52; N, 7.80. Found: C, 55.87; H, 7.69; N, 7.54.

EXAMPLE 58

6-O-[9-(2-Methyl-1,4-naphthoquinon-3-yl)nonanoyl-L-leucyl]-N-acetylmuramyl-α-aminoisobutyryl-D-isoglutamine (46.5 mg, 0.05 mmol) was dissolved in methanol (0.5 ml), and treated with excess ethereal solution of diazomethane in a similar manner to that described in Example 37 to obtain methyl 6-O-[9-(2-methyl-1,4-naphthoquinon-3-yl)-nonanoyl-L-leucyl]-N-acetylmuramyl-α-aminoisobutyryl-D-isoglutaminate (39.8 mg). $[\alpha]_D^{21}$ +20.8° (C 0.5, ethanol). $R_f^1=0.66$.

Elemental analysis for $C_{47}H_{69}O_{15}N_5 \cdot H_2O$: Calculated: C, 58.67; H, 7.44; N, 7.28. Found: C, 59.05; H, 7.81; N, 7.13.

EXAMPLE 59

6-O-(Retinoyl-β-alanyl)-N-acetylmuramyl-L-alanyl-D-isoglutamine (42.3 mg, 0.05 mmol) was dissolved in methanol (0.5 ml), and treated with an excess ethereal solution of diazomethane in a similar manner to that described in Example 37 to obtain methyl 6-O-(retinoyl-β-alanyl)-N-acetylmuramyl-L-alanyl-D-isoglutaminate (31.1 mg). $[\alpha]_D^{22}$ +22.2° (after 25 hours). $R_f^1=0.56$ Elemental analysis for $C_{43}H_{65}O_{13}N_5.3.5H_2O$: Calculated: C, 55.95; H, 7.86; N, 7.59. Found: C, 55.79; H, 7.22; N, 7.41.

EXAMPLE 60

6-O-(QS-3-L-Propionyl)-N-acetylmuramyl-L-alanyl-D-isoglutamine (41.1 mg, 0.05 mmol) was dissolved in methanol (0.5 ml), and treated with an excess ethereal solution of diazomethane in a similar manner to that described in Example 37 to obtain methyl 6-O-(QS-3-L-propionyl)-N-acetylmuramyl-L-alanyl-D-isoglutaminate (32.6 mg). $[\alpha]_D^{21}$ +11.8° (C 0.5, ethanol). $R_f^1 = 0.66$.

Elemental analysis for $C_{37}H_{53}O_{17}N_5.2.5H_2O$: Calculated: C, 50.22; H, 6.61; N, 7.92. Found: C, 50.65; H, 6.35; N, 7.81.

EXAMPLE 61

(I) 1-α-O-Benzyl-4,6-O-benzylidene-N-benzoylmuramic acid (213.4 mg, 0.4 mmol) and HONB (89.6 mg, 0.5 mmol) were dissolved in a mixture of dioxane (3 ml) and ethyl acetate (4 ml). To this solution was added DCC (103.2 mg, 0.5 mmol) under cooling and the reaction mixture was stirred at room temperature for 6 hours. After filtration and evaporation, the resulting 1-α-O-benzyl-4,6-O-benzylidene-N-benzoylmuramic acid HONB ester was dissolved together with methyl L-valyl-D-isoglutaminate hydrochloride (133.1 mg, 0.45 mmol) in DMF (1.5 ml). To this mixture was added NEM (63 μl) and the mixture was stirred at room temperature for 6 hours. After evaporation, the product was reprecipitated from DMF/ethyl acetate to obtain methyl 1-α-O-benzyl-4,6-O-benzylidene-N-benzoylmuramyl-L-valyl-D-isoglutaminate (240 mg). $[\alpha]_D$ +75.4° (C 0.5, DMF). $R_f^3 = 0.41$.

Elemental analysis for $C_{41}H_{50}O_{11}N_4$: Calculated: C, 63.55; H, 6.51; N, 7.23. Found: C, 63.47; H, 6.58; N, 7.09.

(II) Methyl 1-α-O-benzyl-4,6-O-benzylidene-N-benzoylmuramyl-L-valyl-D-isoglutaminate (193.7 mg, 0.25 mmol) was dissolved in 80% acetic acid (2.5 ml) and heated on a boiling water bath for 15 minutes. After evaporation, the residue was reprecipitated from ethanol/ether to obtain methyl 1-α-O-benzyl-N-benzoylmuramyl-L-valyl-D-isoglutaminate (138.5 mg). $[\alpha]_D$ +69.2° (C 0.5, DMF). $R_f^4 = 0.49$ Elemental analysis for $C_{34}H_{46}O_{11}N_4$: Calculated: C, 59.46; H, 6.75; N, 8.16. Found: C, 59.28; H, 6.73; N, 8.10.

(III) Methyl 1-α-O-benzyl-N-benzoylmuramyl-L-valyl-D-isoglutaminate (103 mg, 0.15 mmol), QS-10-OH p-nitrophenyl ester (142.1 mg, 0.3 mmol) and HOBt (158.5 mg, 1.2 mmol) were dissolved in DMF (1 ml). To this solution was added NEM (153.6 μl, 1.2 mmol) and the mixture was stirred at room temperature for two days. After evaporation, the residue was reprecipitated from ethanol/ether. Further, the product was purified by the column chromatography on a silica gel column with chloroform/methanol (19:1, v/v) as eluent to obtain methyl 1-α-O-benzyl-6-O-(QS-10)-N-benzoylmuramyl-L-valyl-D-isoglutaminate (53.8 mg), $[\alpha]_D$ +39.6° (C 0.5, ethanol). $R_f^2 = 0.89$, $R_f^3 = 0.25$, $R_f^4 = 0.78$.

Elemental analysis for $C_{48}H_{68}O_{17}N_4$: Calculated: C, 59.24; H, 7.04; N, 5.76. Found: C, 59.60; H, 7.21; N, 5.89.

EXAMPLE 62

10-(2,3-Dimethoxy-5-methyl-1,4-benzoquinon-6-yl)-10-oxodecanoic acid (146.6 mg, 0.4 mmol) and p-nitrophenol (55.6 mg, 0.44 mmol) were dissolved in acetonitrile (2 ml). To this mixture was added DCC (82.6 mg, 0.44 mmol) under ice-cooling and the mixture was stirred at room temperature for 16 hours. The insoluble material was filtered and the solvent was removed. The resulting 10-(2,3-dimethoxy-5-methyl-1,4-benzoquinon-6-yl)-10-oxo-decanoic acid p-nitrophenyl ester was dissolved together with methyl 1-α-O-benzyl-N-acetylmuramyl-L-valyl-D-isoglutaminate (124.8 mg, 0.4 mmol) and HOBt (108.1 mg, 0.8 mmol) in DMF (0.75 ml). To this solution was added NEM (102.4 μl, 0.8 mmol) and the mixture was stirred at room temperature for 48 hours. After evaporation the purification in a similar manner to that described in Example 6 (V) gave methyl 1-α-O-benzyl-6-O-[10-(2,3-dimethoxy-5-methyl-1,4-benzoquinon-6-yl)-10-oxo-decanoyl]-N-acetylmuramyl-L-valyl-D-isoglutaminate (81.4 mg). $[\alpha]_D^{21}$ +73.1° (C 0.5, ethanol). $R_f^2 = 0.59$.

Elemental analysis for $C_{48}H_{68}O_{17}N_4.\frac{1}{2}H_2O$: Calculated: C, 58.70; H, 7.08; N, 5.71. Found: C, 58.99; H, 7.30; N, 5.69.

EXAMPLE 63

(I) 1-α-O-Benzyl-N-acetylmuramic acid (1.53 g, 4 mmol) was dissolved in pyridine (8 ml), and triphenylchloromethane (2.34 g, 8.4 mmol) was added. After being stirred at 40° C. for 15 hours, the reaction mixture was poured onto ice-water (100 ml). Acetic acid (20 ml) was then added, followed by the extraction with ethyl acetate (50 ml×2). The combined ethyl acetate layer was washed thoroughly with water, dried over anhydrous sodium sulfate and evaporated. The residue was triturated with ether/petroleum ether to obtain 1-α-O-benzyl-6-O-trityl-N-acetylmuramic acid (2.30 g). m.p. 135°–137° C. $[\alpha]_D^{21}$ +82.7° (C 0.5, DMF). $R_f^2 = 0.69$.

Elemental analysis for $C_{37}H_{39}O_8N.\frac{1}{2}H_2O$: Calculated: C, 70.01; H, 6.35; N, 2.21. Found: C, 70.07; H, 6.44; N, 2.13.

(II) 1-α-O-Benzyl-6-O-trityl-N-acetylmuramic acid (2.10 g, 3.4 mmol) was dissolved in DMF (20 ml). To this solution was added carefully sodium hydride (60% in oil; 300 mg, 7.48 mmol) at 60° C. under nitrogen, and then the mixture was stirred at the same temperature for 30 minutes. Then, methyl iodide (0.233 ml, 3.74 mmol) was added under ice-cooling and the mixture was stirred at room temperature for 15 hours. Water (50 ml) was added carefully to the reaction mixture, which was then acidified with acetic acid, extracted with ethyl acetate (50 ml). The ethyl acetate layer was washed with water, dried over anhydrous sodium sulfate and evaporated. The residue was purified by the column chromatography on silica gel (column size: 4×12 cm elution solvent: the same solvent system as that for $R_f^4$). The fractions containing the pure product were collected and the solvent was removed. The residue was triturated with ether/petroleum ether to obtain 1-α-O-benzyl-4-O-methyl-6-O-trityl-N-acetylmuramic acid (1.43 g). m.p. 109°–111° C. (dec.). $[\alpha]_D^{21}$ +102.2° (C 0.5, DMF). $R_f^2 = 0.73$ Elemental analysis for $C_{38}H_{41}O_8N$: Calculated: C, 71.34; H, 6.46; N, 2.19. Found: C, 71.37; H, 6.72; N, 2.01.

(III) 1-α-O-Benzyl-4-O-methyl-6-O-trityl-N-acetylmuramic acid (320 mg, 0.5 mmol) and HONB (108 mg, 0.6 mmol) were dissolved in acetonitrile (5 ml). To this solution was added DCC (124 mg, 0.6 mmol) under ice-cooling. The mixture was stirred at 0° for one hour and then at room temperature for 3 hours. After filtration, methyl L-valyl-D-isoglutaminate hydrochloride (148 mg, 0.5 mmol) was added together with TEA (0.07 ml) to the filtrate. The mixture was then stirred at room temperature for 48 hours and evaporated. The residue was dissolved in ethyl acetate (30 ml), washed with a 5% aqueous citric acid solution, a 5% aqueous sodium bicarbonate solution and water successively, dried over anhydrous sodium sulfate, and evaporated. The residue was crystallized from ether to obtain methyl 1-α-O-benzyl-4-O-methyl-6-O-trityl-N-acetylmuramyl-L-valyl-D-isoglutaminate (375 mg). m.p. 125°–127° C. $[\alpha]_D^{21}$ +78.3° (C 0.5, DMF). $R_f^2 = 0.77$, $R_f^4 = 0.69$.

Elemental analysis for $C_{49}H_{60}O_{11}N_4$: Calculated: C, 66.80; H, 6.86; N, 6.36. Found: C, 67.21; H, 7.17; N, 6.29.

(IV) Methyl 1-α-O-benzyl-4-O-methyl-6-O-trityl-N-acetylmuramyl-L-valyl-D-isoglutaminate (345 mg, 0.39 mmol) was dissolved in 80% acetic acid (20 ml) and heated at 100° C. for 20 minutes. The solution was concentrated and water (15 ml) was added. After filtration and evaporation, the residue was flushed with water and then with toluene twice. The crystalline residue was washed with hot methanol to obtain methyl 1-α-O-benzyl-4-O-methyl-N-acetylmuramyl-L-valyl-D-isoglutaminate (152 mg). m.p. >245° C. $[\alpha]_D^{21}$ +111.6° (C 0.5, DMF). $R_f^2 = 0.52$, $R_f^4 = 0.40$.

Elemental analysis for $C_{30}H_{46}O_{11}N_4$: Calculated: C, 56.41; H, 7.26; N, 8.77. Found: C, 56.17; H, 7.16; N, 8.66.

(V) Methyl 1-α-O-benzyl-4-O-methyl-N-acetylmuramyl-L-valyl-D-isoglutaminate (68 mg, 0.106 mmol) and QS-10-OH (40.4 mg, 0.128 mmol) were dissolved in a mixture of pyridine (0.6 ml) and DMF (0.6 ml). To this solution was added DCC (32.8 mg, 0.16 mmol). The mixture was then stirred at room temperature for 48 hours and evaporated. The residue was purified by the column chromatography on a silica gel (column size: 1.5×12 cm; elution solvent: methanol/chloroform=5:95). The fractions containing the desired product were collected and the solvent was removed. The resulting crystals were recrystallized from chloroform/ether to obtain methyl 1-α-O-benzyl-4-O-methyl-6-O-(QS-10)-N-acetylmuramyl-L-valyl-D-isoglutaminate (40 mg). m.p. 214° C. $[\alpha]_D^{22}$ +72.1° (C 0.4, methanol). $R_f^2 = 0.78$, $R_f^3 = 0.14$, $R_f^4 = 0.69$.

Elemental analysis for $C_{49}H_{72}O_{16}N_4$: Calculated: C, 60.48; H, 7.46; N, 5.76. Found: C, 60.55; H, 7.40; N, 5.66.

EXAMPLE 64

Methyl 1-α-O-benzyl-4-O-methyl-6-O-(QS-10)-N-acetylmuramyl-L-valyl-D-isoglutaminate (25 mg, 0.026 mmol) was catalytically hydrogenated in methanol/acetic acid (5 ml/0.5 ml) using palladium black as a catalyst at room temperature for 3 hours. The catalyst was filtered and the solvent was evaporated. The residue was dissolved in methanol (3 ml). To this solution was added a solution of ferric chloride (300 mg) in water (0.3 ml) and the mixture was stirred at room temperature for 30 minutes. After evaporation the residue was dissolved in ethyl acetate (15 ml) which was washed with a minor amount of water. The ethyl acetate layer was dried over anhydrous sodium sulfate and evaporated. The residue was purified by the column chromatography on Sephadex LH-20 (column size: 1.5×45 cm, elution solvent: 0.1 N acetic acid/ethanol=2:3). The fractions containing the desired product were collected and the solvent was removed. The residue was flushed with ethanol twice. Petroleum ether was added and the resulting crystals were filtered to obtain methyl 4-O-methyl-6-O-(QS-10)-N-acetylmuramyl-L-valyl-D-isoglutaminate (13 mg). m.p. 201° C. $[\alpha]_D^{20}$ +40.8° (C 0.4, methanol). $R_f^1 = 0.89$, $R_f^2 = 0.52$, $R_f^4 = 0.52$.

Elemental analysis for $C_{42}H_{66}O_{16}N_4$: Calculated: C, 57.13; H, 7.53; N, 6.35. Found: C, 57.01; H, 7.78; N, 6.52.

EXAMPLE 65

11-Phenoxyundecanoic acid (45.9 mg, 0.165 mmol) and methyl 1-α-O-benzyl-N-acetylmuramyl-L-valyl-D-isoglutaminate (93.7 mg, 0.15 mmol) were dissolved in a mixture of DMF (0.6 ml) and pyridine (0.6 ml). To this solution was added DCC (46.4 mg, 0.23 mmol). The mixture was stirred at room temperature for 15 hours. After filtration and evaporation, the residue was purified in a similar manner as described in Example 63 (V) by the column chromatography on a silica gel column to obtain methyl 1-α-O-benzyl-6-O-(11-phenoxyundecanoyl)-N-acetylmuramyl-L-valyl-D-isoglutaminate (79 mg). m.p. 190°–193° C. $[\alpha]_D^{22}$ +73.6° (C 0.5, DMF). $R_f^3 = 0.23$.

Elemental analysis for $C_{46}H_{68}O_{13}N_4$: Calculated: C, 62.42; H, 7.74; N, 6.33; Found: C, 62.24; H, 7.66; N, 6.21.

EXAMPLE 66

Methyl 1-α-O-benzyl-6-O-(11-phenoxyundecanoyl)-N-acetylmuramyl-L-valyl-D-isoglutaminate (50 mg, 0.056 mmol) was catalytically hydrogenated in methanol/acetic acid (5.0 ml/0.5 ml) using palladium black as a catalyst at room temperature for 5 hours. The catalyst was filtered and the solvent was removed. The residue was purified by the column chromatography on a Sephadex LH-20 column (column size: 1.5×45 cm; elution solvent: ethanol/0.1 N acetic acid=3:2). The fractions containing the desired product were collected and the solvent was removed. The residue was flushed with ethanol twice and the resulting crystals were recrystallized from ether/ethanol to obtain methyl 6-O-(11-phenoxyundecanoyl)-N-acetylmuramyl-L-valyl-D-isoglutaminate (34 mg). m.p. 189° C. (dec.). $[\alpha]_D^{22}$ +41.4° (C 0.4, methanol). $R_f^2 = 0.36$, $R_f^4 = 0.51$.

Elemental analysis for $C_{39}H_{62}O_{13}N_4$: Calculated: C, 58.92; H, 7.86; N, 7.05. Found: C, 58.66; H, 8.04; N, 6.72.

EXAMPLE 67

Two milligrams of methyl 2-{2-acetamido-2-deoxy-6-O-[10-(2,3-dimethoxy-5-methyl-1,4-benzoquinon-6-yl)decanoyl]-D-glucopyranos-3-O-yl}-D-propionyl-L-valyl-D-isoglutaminate was treated with 10 μg of squalene, and vigorously homogenized with 1 ml of phosphate-buffered saline or 1 ml of saline containing 0.2% Tweene 80 to obtain an oil-in-water emulsion. This product is useful for parenteral administration.

EXAMPLE 68

Eight milligrams of methyl 2-{2-acetamido-2-dexoy-6-O-[10-(2,3-dimethoxy-5-methyl-1,4-benzoquinon-6-yl)decanoylglycol]-D-glucopyranos-3-O-yl}-D-propionyl-L-valyl-D-isoglutaminate was suspended in 3.5 ml of phosphate-buffered saline and sterilized in the usual manner. The resulting suspension was then added dropwise with vigorous stirring to 0.5 ml of a sterilized mixture of a hydrogenated vegetable triglyceride (Migryol 812) and mannitol monooleate (17:3) to obtain an oil-in-water suspension. This produuct is useful for parenteral administration.

EXAMPLE 69

Five hundred milligrams of methyl 2-{2-acetamido-2-deoxy-6-O-[3-(2,3-dimethoxy-5-methyl-1,4-benzoquinon-6-yl)propionyl]-D-glucopyranos-3-O-yl}-D-propionyl-L-Valyl-D-isoglutaminate and 5 g of mannitol were mixed in distilled water. The mixture was then made to a volume of 1000 ml, sterilized in a usual manner, distributed, in 2 ml portions into vials, and freeze-dried. This preparation is diluted in saline to make an injectable solution just prior to use.

What is claimed is:

1. A compound of the formula:

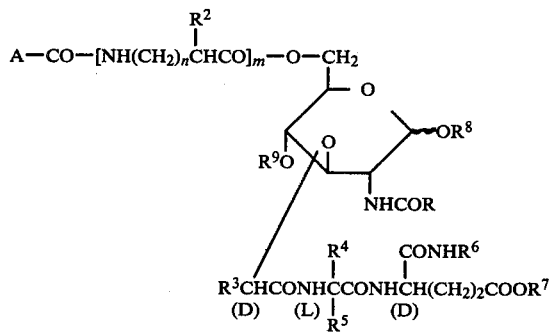

wherein

A is a $C_{2-10}$ acylic hydrocarbon group, the terminal of which is substituted with an unsaturated 6-membered cyclic hydrocarbon group;

m is 0 or 1;

n is 0 or an integer of 1 to 9;

R is $C_{1-4}$ alkyl which may be substituted with hydroxyl, or phenyl;

$R^2$ is hydrogen or $C_{1-4}$ alkyl which may form a ring by connecting its terminal with the α-nitrogen atom, when n is 0, or hydrogen when n is an integer of 1 to 9;

$R^3$ is hydrogen or $C_{1-4}$ alkyl;

$R^4$ and $R^5$ are each hydrogen or $C_{1-4}$ alkyl which may be substituted with hydroxyl or benzyloxyl;

$R^6$ is hydrogen or $C_{1-4}$ alkyl;

$R^7$ is $C_{1-18}$ alkyl which may be substituted with $C_{1-3}$ alkoxyl;

$R^8$ and $R^9$ are each hydrogen, $C_{1-4}$ alkyl or $C_{1-2}$ alkyl substituted with phenyl; and (D) and (L) each indicate configuration if their respective carbon atoms are asymmetric;

or an acid addition salt thereof.

2. A compound according to claim 1, wherein m is 0.

3. A compound according to claim 1, wherein m is 1 and n is 0.

4. A compound according to claim 1, wherein $R^7$ is $C_{1-4}$ alkyl.

5. A compound of the formula:

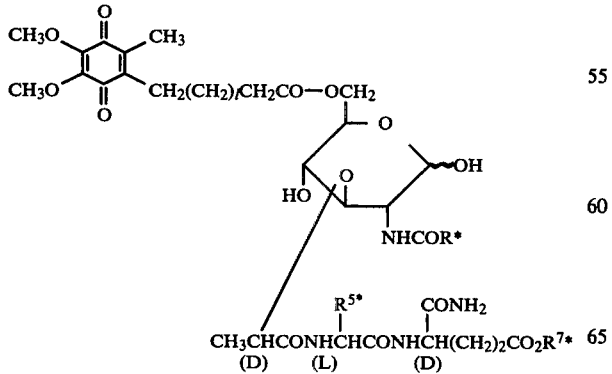

wherein l is an integer of 0 to 7;

$R^*$ is $C_{1-4}$ alkyl;

$R^{5*}$ is $C_{1-4}$ alkyl which may be substituted with hydroxyl;

$R^{7*}$ is $C_{1-4}$ alkyl;

or an acid addition salt thereof.

6. A compound according to claim 1, wherein $R^8$ and $R^9$ are each hydrogen.

7. A compound according to claim 1, said compound being methyl 2-[2-acetamido-2-deoxy-6-O-{10-(2,3-dimethoxy-5-methyl-1,4-benzoquinon-6-yl)decanyl}-D-glucopyranos-3-O-yl]-D-propionyl-L-valyl-D-isoglutaminate.

8. A compound according to claim 1, said compound being methyl 2-[2-acetamido-2-deoxy-6-O-{10-(2,3-dimethoxy-5-methyl-1,4-benzoquinon-6-yl)decanoyl}-D-glucopyranos-3-O-yl]-D-propionyl-L-seryl-D-isoglutaminate.

9. A compound according to claim 1, said compound being methyl 2-[2-acetamido-2-deoxy-6-O-{10-(2,3-dimethoxy-5-methyl-1,4-benzoquinon-6-yl)decanoyl}glycyl-D-glucopyranos-3-O-yl]-D-propionyl-L-valyl-D-isoglutaminate.

10. A method for stimulating the immunological functions of a warmblooded animal which comprises administering to said animal an effective amount of a compound of the formula:

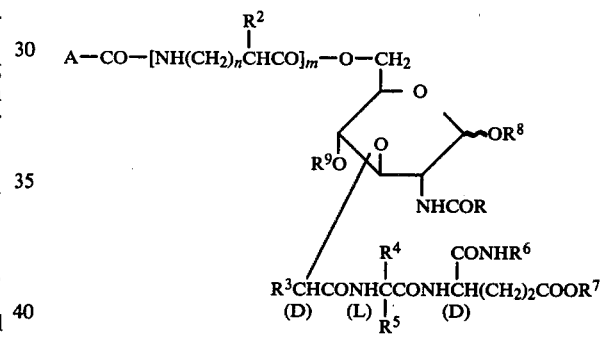

wherein

A is a $C_{2-10}$ acylic hydrocarbon group, the terminal of which is substituted with an unsaturated 6-membered cyclic hydrocarbon group;

m is 0 or 1;

n is 0 or an integer of 1 to 9;

R is $C_{1-4}$ alkyl which may be substituted with hydroxyl, or phenyl;

$R^2$ is hydrogen or $C_{1-4}$ alkyl which may form a ring by connecting its terminal with the α-nitrogen atom, when n is 0, or hydrogen when n is an integer of 1 to 9;

$R^3$ is hydrogen or $C_{1-4}$ alkyl;

$R^4$ and $R^5$ are each hydrogen or $C_{1-4}$ alkyl which may be substituted with hydroxyl or benzyloxyl;

$R^6$ is hydrogen or $C_{1-4}$ alkyl;

$R^7$ is $C_{1-18}$ alkyl which may be substituted with $C_{1-3}$ alkoxyl;

$R^8$ and $R^9$ are each hydrogen, $C_{1-4}$ alkyl or $C_{1-2}$ alkyl substituted with phenyl; and (D) and (L) each indicate configurations if their respective carbon atoms are asymmetric;

or an acid addition salt thereof.

11. A compound defined as in claim 1, but wherein A-CO is 10-(2,3-dimethoxy-5-methyl-1,4-benzoquinn-6-yl)decanoyl.